US009732366B2

(12) United States Patent
Okuma et al.

(10) Patent No.: US 9,732,366 B2
(45) Date of Patent: Aug. 15, 2017

(54) THERMOSTABLE XYLANASE BELONGING TO GH FAMILY 10

(71) Applicant: HONDA MOTOR CO., LTD., Minato-ku, Tokyo (JP)

(72) Inventors: Jiro Okuma, Wako (JP); Yoshitsugu Hirose, Wako (JP); Asuka Yamaguchi, Tokyo (JP); Migiwa Suda, Kisarazu (JP); Yasuhiro Kondo, Kawagoe (JP); Tomohiko Kato, Kisarazu (JP); Daisuke Shibata, Kisarazu (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 14/837,706

(22) Filed: Aug. 27, 2015

(65) Prior Publication Data

US 2016/0060666 A1 Mar. 3, 2016

(30) Foreign Application Priority Data

Aug. 29, 2014 (JP) ................................ 2014-175186

(51) Int. Cl.
*C12N 9/24* (2006.01)
*C12P 19/14* (2006.01)
(Continued)

(52) U.S. Cl.
CPC ................ *C12P 19/14* (2013.01); *C12N 1/14* (2013.01); *C12N 1/16* (2013.01); *C12N 1/20* (2013.01); *C12N 9/248* (2013.01); *C12N 9/2434* (2013.01); *C12N 15/63* (2013.01); *C12P 19/02* (2013.01); *C12Y 302/01008* (2013.01); *D21C 5/005* (2013.01); *D21H 17/005* (2013.01); *C12Y 302/01037* (2013.01)

(58) Field of Classification Search
None
See application file for complete search history.

(56) References Cited

U.S. PATENT DOCUMENTS 5,395,765 A 3/1995 Dahlberg et al.
5,688,668 A 11/1997 Sjoholm et al.
(Continued)

FOREIGN PATENT DOCUMENTS

JP 2004121257 A 4/2004

OTHER PUBLICATIONS

GenSeq Accession No. ADJ34934, published Apr. 22, 2004.*
(Continued)

*Primary Examiner* — Robert Mondesi
*Assistant Examiner* — Richard Ekstrom
(74) *Attorney, Agent, or Firm* — Carrier Blackman & Associates, P.C.; Joseph P. Carrier; Fulchand P. Shende

(57) ABSTRACT

A thermostable xylanase having a xylanase catalytic domain including: (A) a polypeptide including the amino acid sequence represented by SEQ ID NO: 1, (B) a polypeptide including an amino acid sequence in which at least one amino acid has been deleted, substituted, or added in the amino acid sequence represented by SEQ ID NO: 1, and having xylanase activity at least under conditions of 85° C. and pH 6.0, or (C) a polypeptide including an amino acid sequence having 80% or greater sequence identity with the amino acid sequence represented by SEQ ID NO: 1, and having xylanase activity at least under conditions of 85° C. and pH 6.0.

18 Claims, 5 Drawing Sheets

```
AR19M-177-21        1 MGVKSVKKLLVAFLLSLLTLGLASNGLEGETLRSLAEKLGIYVGFASINNFWVLADGSTY  60
Thermotoga sp. R02  1 -------MKILPSVLILLLG-CVPVFSSQNVSLRELAEKLNIYVGFAAINNFWSLSDAEKY  53

AR19M-177-21       61 MEVAKREFNILTPENHMKWDSIHPERDRYDFSKAERHVKFALENGMVVHGHTLVWHNQLP 120
Thermotoga sp. R02 54 MEVARREFNILTPENQMKWDTIHPERDRYNFTPAEKHVEFAEENNMIVHGHTLVWHNQLP 113

AR19M-177-21      121 PWLN-KEWTKEELLQVLEEHIKTVVGYFKGKVKIWDVVNEAVSDAGRYRETIWYKVIGPE 179
Thermotoga sp. R02 114 GWITGREWTKEELLNVLEDHIKTVVSHFKGRVKIWDVVNEAVSDSGTYRESIWYKTIGPE 173

AR19M-177-21      180 YIEKAFIWAREADPDATLIYNDYNIETINPKSNFVYQLVKELKEKGVPIDGVGFQMHIDI 239
Thermotoga sp. R02 174 YIEKAFRWAKEADPDAILIYNDYSIEEINAKSNFVYNMIKELKEKGVPVDGIGFQMHIDY 233

AR19M-177-21      240 NGINYESFRNNLKRFADLGLKLYITEMDVRIPKNATQEH-LQKQAEIYAKIFEICLENPA 298
Thermotoga sp. R02 234 RGLNYDSFRRNLERFAKLGLQIYITEMDVRIPLSGSEEYYLKKQAEVCAKIFDICLDNPA 293

AR19M-177-21      299 VEAIQFWGFTDKYSWVPGFFTGYDHALIFDRDYNPKPAYFAIKQVLAKKLEEKLKGK    355
Thermotoga sp. R02 294 VKAIQFWGFTDKYSWVPGFFKGYGKALLFDENYNPKPCYYAIKEVLEKKIEERK---    347
```

(51) Int. Cl.

| | |
|---|---|
| ***C12N 1/20*** | (2006.01) |
| ***C12N 1/14*** | (2006.01) |
| ***C12N 15/63*** | (2006.01) |
| ***C12N 1/16*** | (2006.01) |
| ***C12N 9/42*** | (2006.01) |
| ***C12P 19/02*** | (2006.01) |
| ***D21C 5/00*** | (2006.01) |
| ***D21H 17/00*** | (2006.01) |

(56) References Cited

U.S. PATENT DOCUMENTS 5,759,840 A 6/1998 Sung et al.
5,866,408 A 2/1999 Sung et al.
5,902,581 A 5/1999 Clarkson et al.
6,083,733 A 7/2000 Gronberg et al.
7,060,482 B1 6/2006 Sung et al.
7,851,193 B2 * 12/2010 Lopez de Leon .......................... C12N 15/8245 435/200
2006/0003433 A1 1/2006 Steer et al.
2006/0014247 A1 1/2006 Paloheimo et al.
2010/0062511 A1 3/2010 Clarkson et al.

OTHER PUBLICATIONS

Extended European Search Report for European Application 15182761.5 mailed Jan. 11, 2016.

Database Protein [Online]/Anonymous, “1, 4-beta-xylanase [*Thermotoga hypogea*] GI:671519753”, Aug. 5, 2014, XP002751778, retrieved from NCBI Database accession No. WP_031505017.1.

Database Protein [Onine]/Anonymous, “1, 4-beta-xylanase [*Thermotoga hypogea*] GI:671519753”, XP002751779, Jan. 30, 2015, retrieved from NCBI Database accession No. WP_041077403.1.

Mori et al., “*Thermotoga profunda* sp. nov. and *Thermotoga caldifontis* sp. nov., anaerobic thermophilic bacteria solated from terrestrial hot springs”, International Journal of Systematic and Evolutionary Microbiology, Mar. 27, 2015, vol. 64, No. Pt 6, pp. 2128-2136, XP055232559, GB ISSN: 1466-5026, DOI: 10.1099/ijs.0.060137-0.

Sunna et al., “A novel thermostable multidomain 1,4-[beta]-xylanase from ‘Caldibacillus cellulovorans’ and effect of its Kylan-binding domain on enzyme activity”, Microbiology vol. 146, No. 11, Nov. 1, 2000, pp. 2947-2955, KP055232570, GB ISSN: 1350-0872, DOI: 10.1099/00221287-146-11-2947.

Luo et al., “A thermophilic and acid stable family-10 xylanase from the acidophilic fungus *Bispora* sp. MEY-1”, Extremophiles, vol. 13, No. 5, Aug. 5, 2009, pp. 849-857, XP019742659, Life Under Extreme Conditions, Springer-Verlag, to ISSN: 1433-4909, DOI:10.1007/S00792-009-0272-0.

Ray et al., “Production and characterization of xylanase from a beta-amylolytic strain of Bacillus megaterium”, Microbios, vol. 90, No. 362, Jan. 1, 1997, pp. 7-16, XP009187475, Cambridge, GB ISSN: 0026-2633.

Zhengqiang, et al., “Characterization of a Thermostable Family 10 Endo-Xylanase (XynB) from Thermotoga maritima That Cleaves p-Nitrophenyl-Beta-D-Xyloside”, Journal of Bioscience and Bio-engineering, 2001, vol. 92, pp. 423-428, Tsukuba, Ibaraki, Japan.

Winterhalter, et al., “Two Extremely Thermostable Xylanases of the Hyperthermophilic Bacterium Thermotoga maritima MSB8”, Applied and Environmental Microbiology, 1995, vol. 61, pp. 1810-1815, Munich, Federal Republic of Germany.

Yoon, et al., “Expression of Thermotoga maritima Endo-Beta-1, 4-xylanase Gene in *E. coli* and Characterization of the Recombinant Enzyme” Agricultural Chemistry & Biotechnology, 2004, vol. 47, pp. 157-160, Cheongju, Korea.

Kishishita et al., “Cellulose-inducible xylanase Xyl10A from Acremonium cellulolyticus: Purification, cloning and homologous expression”, Protein Expression and Purification, 2014, vol. 94, pp. 40-45, Golden, Colorado, USA.

Noguchi et al., “MetaGeneAnnotator: Detecting Species-Specific Patterns of Binding Site for Precise Gene Prediction in Anonymous Prokaryotic and Phage Genomes”, DNA Research, 2008, vol. 15, pp. 387-396, Chiyoda-ku, Tokyo, Japan.

Finn et al., “The Pfam protein families database”, Nucleic Acids Research, 2010, vol. 38, pp. D211-D222, Helsinki, Finland.

Durbin et al., The Theory Behind Profile HMMs Biological sequence analysis: Probabilistic models of proteins and nucleic acids, 1998, Cambridge University Press.

“Annex of *Thermotoga profunda* sp. nov. and *Thermotoga caldifontis* sp. nov., anaerobic thermophilic bacteria isolated from terrestrial hot springs”, International Journal of Systematic and Evolutionary Microbiology, vol. 64.

Office Action, dated May 31, 2017, issued in the corresponding European Patent Application 15 182 761.5.

* cited by examiner

FIG. 1

```
AR19M-177-21         1 MGVKSVKKLLVAFLLSLLTLGLASNGLEGETLRSLAEKLGIYVGFASINNFWVLADGSTY  60
Thermotoga sp. RQ2   1 ------MKILPSVLILLLG-CVPVFSSQNVSLRELAEKLNIYVGFAAINNFWSLSDAEKY  53

AR19M-177-21        61 MEVAKREFNILTPENHMKWDSIHPERDRYDFSKAERHVKFALENGMVVHGHTLVWHNQLP 120
Thermotoga sp. RQ2  54 MEVARREFNILTPENQMKWDTIHPERDRYNFTPAEKHVEFAEENNMIVHGHTLVWHNQLP 113

AR19M-177-21       121 PWLN-KEWTKEELLQVLEEHIKTVVGYFKGKVKIWDVVNEAVSDAGRYRETIWYKVIGPE 179
Thermotoga sp. RQ2 114 GWITGREWTKEELLNVLEDHIKTVVSHFKGRVKIWDVVNEAVSDSGTYRESIWYKTIGPE 173

AR19M-177-21       180 YIEKAFIWAREADPDATLIYNDYNIETINPKSNFVYQLVKELKEKGVPIDGVGFQMHIDI 239
Thermotoga sp. RQ2 174 YIEKAFRWAKEADPDAILIYNDYSIEEINAKSNFVYNMIKELKEKGVPVDGIGFQMHIDY 233

AR19M-177-21       240 NGINYESFRNNLKRFADLGLKLYITEMDVRIPKNATQEH-LQKQAEIYAKIFEICLENPA 298
Thermotoga sp. RQ2 234 RGLNYDSFRRNLERFAKLGLQIYITEMDVRIPLSGSEEYYLKKQAEVCAKIFDICLDNPA 293

AR19M-177-21       299 VEAIQFWGFTDKYSWVPGFFTGYDHALIFDRDYNPKPAYFAIKQVLAKKLEEKLKGK    355
Thermotoga sp. RQ2 294 VKAIQFWGFTDKYSWVPGFFKGYGKALLFDENYNPKPCYYAIKEVLEKKIEERK---    347
```

Differential scanning fluorimetry (DSF)
Fluorescence (A.U.)
4800
4400
4000
3600
3200
2800
2400
- d(Fluorescence)/dT
200
0
-200
-400
-600
-800
-1000
50
60
70
80
90
100
Temperature (°C)
50
60
70
80
90
100
Temperature (°C)

THERMOSTABLE XYLANASE BELONGING TO GH FAMILY 10

TECHNICAL FIELD

The present invention relates to a thermostable xylanase, a polynucleotide encoding the thermostable xylanase, an expression vector for expressing the thermostable xylanase, a transformant into which the expression vector has been incorporated, and a method for producing a lignocellulose degradation product using the thermostable xylanase.

Priority is claimed on Japanese Unpublished Patent Application No. 2014-175186, the content of which is incorporated herein by reference.

BACKGROUND ART

In recent years, as a result of concerns related to energy supplies for transportation, as well as other environmental problems such as global warming and aerial pollution, the development of alternative energy sources to oil has become an extremely important issue. Plant biomass is the most plentiful renewable energy source on earth, and holds great promise as an alternative energy source to oil. The main component of plant biomass (lignocellulose) is composed of polysaccharides such as celluloses and hemicelluloses (including xylan, arabinan and mannan), as well as lignin and pectin and the like. These polysaccharides are hydrolyzed by a large variety of glycoside hydrolases to form monosaccharides such as glucose and xylose, which can then be used as biofuels or the raw materials for chemical products.

Lignocellulose is recalcitrant due to its highly complex structure, and is difficult to degrade or hydrolyze with a single cellulolytic enzyme. Accordingly, among the various polysaccharides, hydrolysis of cellulose generally requires three types of glycoside hydrolase enzymes, namely an endoglucanase (endo-1,4-β-D-glucanase, EC 3.2.1.4), an exo-type cellobiohydrolase (1,4-β-cellobiosidase or cellobiohydrolase, EC 3.2.1.91, EC 3.2.1.176), and a β-glucosidase (EC 3.2.1.21). On the other hand, hemicelluloses include xylan, arabinan, and mannan and the like, and the structure varies depending on the plant. For example, in the case of hardwoods and herbaceous plants, xylan is the main structural component. Hydrolysis of xylan requires a xylanase (endo-1,4-β-xylanase, EC 3.2.1.8) and a β-xylosidase (3.2.1.37).

In conventional bioethanol production using lignocellulose as a starting resource, hydrolysis processes using high solid loading (30 to 60% solid loading) have been tested with the aim of achieving a more energy-efficient conversion to ethanol. However, in this type of lignocellulose enzymatic hydrolysis using high solid loading, the viscosity of the biomass slurry is high, and the hydrolysis reaction of the lignocellulose tends to proceed poorly. Accordingly, by using a thermostable enzyme and performing the enzymatic hydrolysis treatment at a high temperature of 80° C. or higher, the rate of the hydrolysis reaction can be increased, and the viscosity of the biomass slurry can be reduced, which is expected to enable a shortening of the hydrolysis reaction time and a reduction in the amount of enzyme required. As a result, for all of the various glycoside hydrolases, the development of enzymes having superior thermostability is very desirable.

Many thermostable glycoside hydrolases have been obtained by isolating and identifying thermophilic microorganisms that exist in high-temperature environments, cloning genes from these isolated and cultured microorganisms, determining the DNA sequence, and then expressing the DNA using *E. coli* or filamentous fungi or the like. Particularly in the case of xylanases required for the hydrolysis of the hemicellulose xylan, large numbers have already been isolated from thermophiles, filamentous fungi, and Archaea and the like for purposes such as lignocellulose hydrolysis and pulp processes and the like. For example, Patent Document 1 discloses a xylanase derived from *Acidothermus cellulolyticus*, the xylanase exhibiting enzymatic activity at 60 to 80° C. Patent Document 2 discloses a xylanase derived from an anaerobic thermostable bacterium isolated from a New Zealand hot spring, and this xylanase also exhibits enzymatic activity at 60 to 80° C. Patent Document 3 discloses a xylanase derived from a *Bacillus* bacterium isolated from the soil, the xylanase having an optimum temperature of 80° C. Non-Patent Document 4 reports a xylanase derived from *Acremonium cellulolyticus*, the xylanase having an optimum temperature in the vicinity of 60 to 80° C. Tests aimed at further improving the thermostability have also been conducted, and Patent Documents 4 to 7 disclose xylanases for which the thermostability has been improved by substituting amino acids of natural enzymes. Patent Document 8 discloses that by truncating a natural xylanase having an enzymatically active domain and a carbohydrate binding module connected by a linker, by removing either the carbohydrate binding module or the carbohydrate binding module and the linker, production of the enzyme within the host could be increased. Almost all of the above enzymes have optimum temperatures of 60 to 80° C., and further improvements in the thermostability are still required.

On the other hand, Patent Documents 9 and 10 and Non-Patent Documents 1 to 3 disclose examples of hyperthermostable xylanases isolated from specific bacteria and filamentous fungi, and xylanases having an optimum temperature exceeding 85° C. have been reported. Patent Document 9 reports a xylanase with an optimum temperature of 90° C. derived from *Rhodothermus marinus*, but the specific activity at 90° C. is only about 26 nkat/mg protein (=about 1.6 U/mg protein), which is very low.

PRIOR ART LITERATURE

Patent Documents

Patent Document 1: U.S. Pat. No. 5,902,581
Patent Document 2: U.S. Pat. No. 6,083,733
Patent Document 3: Japanese Unexamined Patent Application, First Publication No. 2004-121257
Patent Document 4: U.S. Pat. No. 5,759,840
Patent Document 5: U.S. Pat. No. 5,866,408
Patent Document 6: U.S. Pat. No. 7,060,482
Patent Document 7: U.S. Patent Application No. 2010/0062511
Patent Document 8: U.S. Patent Application No. 2006/0014247
Patent Document 9: U.S. Pat. No. 5,395,765
Patent Document 10: U.S. Pat. No. 5,688,668

Non-Patent Documents

Non-Patent Document 1: Zhengqiang et al., Journal of Bioscience and Bioengineering, 2001, vol. 92, pp. 423 to 428.
Non-Patent Document 2: Winterhalter and Liebl, Applied and Environmental Microbiology, 1995, vol. 61, pp. 1810 to 1815.

Non-Patent Document 3: Yoon et al., Agricultural Chemistry and Biotechnology, 2004, vol. 47, pp. 157 to 160.

Non-Patent Document 4: Kishishita et al., Protein Expression and Purification, 2014, vol. 94, pp. 40 to 45.

SUMMARY OF THE INVENTION

Problems to be Solved by the Invention

The present invention has an object of providing a novel thermostable xylanase that exhibits xylanase activity at least under conditions of 85° C. and pH 6.0, a polynucleotide encoding the thermostable xylanase, an expression vector for expressing the thermostable xylanase, a transformant into which the expression vector has been incorporated, and a method for producing a lignocellulose degradation product using the thermostable xylanase.

Means for Solving the Problem

In order to achieve the above object, the inventors of the present invention extracted DNA directly from the high-temperature soils of hot springs, and by carrying out a large-scale metagenomic sequencing of the microbial flora that was difficult to culture, they succeeded in obtaining a thermostable xylanase having a novel amino acid sequence, thus enabling them to complete the present invention.

In other words, a thermostable xylanase, a polynucleotide, an expression vector, a transformant, a method for producing the thermostable xylanase, a glycoside hydrolase mixture, and a method for producing a lignocellulose degradation product according to the present invention have the aspects [1] to [10] described below.

[1] A thermostable xylanase, having a xylanase catalytic domain including:

(A) a polypeptide including the amino acid sequence represented by SEQ ID NO: 1, (B) a polypeptide including an amino acid sequence in which at least one amino acid has been deleted, substituted, or added in the amino acid sequence represented by SEQ ID NO: 1, and having xylanase activity at least under conditions of 85° C. and pH 6.0, or (C) a polypeptide including an amino acid sequence having 80% or greater sequence identity with the amino acid sequence represented by SEQ ID NO: 1, and having xylanase activity at least under conditions of 85° C. and pH 6.0.

[2] The thermostable xylanase according to [1], which exhibits xylanase activity at pH 6.0 and a temperature of 60 to 90° C.

[3] A polynucleotide, having a region encoding a xylanase catalytic domain, the region including:

(a) a nucleotide sequence encoding a polypeptide including the amino acid sequence represented by SEQ ID NO: 1, (b) a nucleotide sequence encoding a polypeptide which includes an amino acid sequence in which at least one amino acid has been deleted, substituted, or added in the amino acid sequence represented by SEQ ID NO: 1, and has xylanase activity at least under conditions of 85° C. and pH 6.0, (c) a nucleotide sequence encoding a polypeptide which includes an amino acid sequence having 80% or greater sequence identity with the amino acid sequence represented by SEQ ID NO: 1, and has xylanase activity at least under conditions of 85° C. and pH 6.0, (d) a nucleotide sequence, having 80% or greater sequence identity with a nucleotide sequence represented by SEQ ID NO: 2, and encoding a polypeptide that has xylanase activity at least under conditions of 85° C. and pH 6.0, or (e) a nucleotide sequence of a polynucleotide which hybridizes with a polynucleotide including the nucleotide sequence represented by SEQ ID NO: 2 under stringent conditions, the nucleotide sequence encoding a polypeptide having xylanase activity at least under conditions of 85° C. and pH 6.0.

[4] The polynucleotide according to [3], wherein the polypeptide exhibits xylanase activity at pH 6.0 and a temperature of 60 to 90° C.

[5] An expression vector incorporating the polynucleotide according to [3] or [4], the expression vector being capable of expressing a polypeptide having xylanase activity in a host cell.

[6] A transformant into which the expression vector according to [5] has been introduced.

[7] The transformant according to [6], which is a eukaryote.

[8] A method for producing a thermostable xylanase, the method including generating the thermostable xylanase in the transformant according to [6] or [7].

[9] A glycoside hydrolase mixture, including the thermostable xylanase according to [1] or [2], a thermostable xylanase encoded by the polynucleotide according to [3] or [4], or a thermostable xylanase produced by the method for producing a thermostable xylanase according to [8], and at least one other glycoside hydrolase.

[10] A method for producing a lignocellulose degradation product, the method including generating the lignocellulose degradation product by bringing a lignocellulose-containing material containing hemicellulose including xylan into contact with the thermostable xylanase according to [1] or [2], a thermostable xylanase encoded by the polynucleotide according to [3] or [4], the transformant according to [6] or [7], a thermostable xylanase produced by the method for producing a thermostable xylanase according to [8], or the glycoside hydrolase mixture according to [9].

Effects of the Invention

The thermostable xylanase according to the present invention has xylanase activity at least under conditions of 85° C. and pH 6.0. For this reason, the thermostable xylanase is suitable for hydrolysis processes of materials containing lignocellulose under high-temperature conditions, and specifically, is ideal for a hydrolysis process of a lignocellulose-containing material containing hemicellulose including xylan.

Further, the polynucleotide according to the present invention, an expression vector incorporating the polynucleotide, and a transformant into which the expression vector has been introduced can be used favorably in the production of the thermostable xylanase according to the present invention.

BRIEF DESCRIPTION OF THE DRAWINGS

FIG. 1 is an amino acid sequence alignment diagram of the amino acid sequence (SEQ ID NO: 1) of a polypeptide (AR19M-177-21) encoded by the gene clone AR19M-177-21, and the amino acid sequence (SEQ ID NO: 6) of an endo-1,4-β-xylanase from the bacterium *Thermotoga* sp. RQ2 of the phylum Thermotogae.

DETAILED DESCRIPTION OF THE INVENTION

[Thermostable Xylanase]

Figure 2:
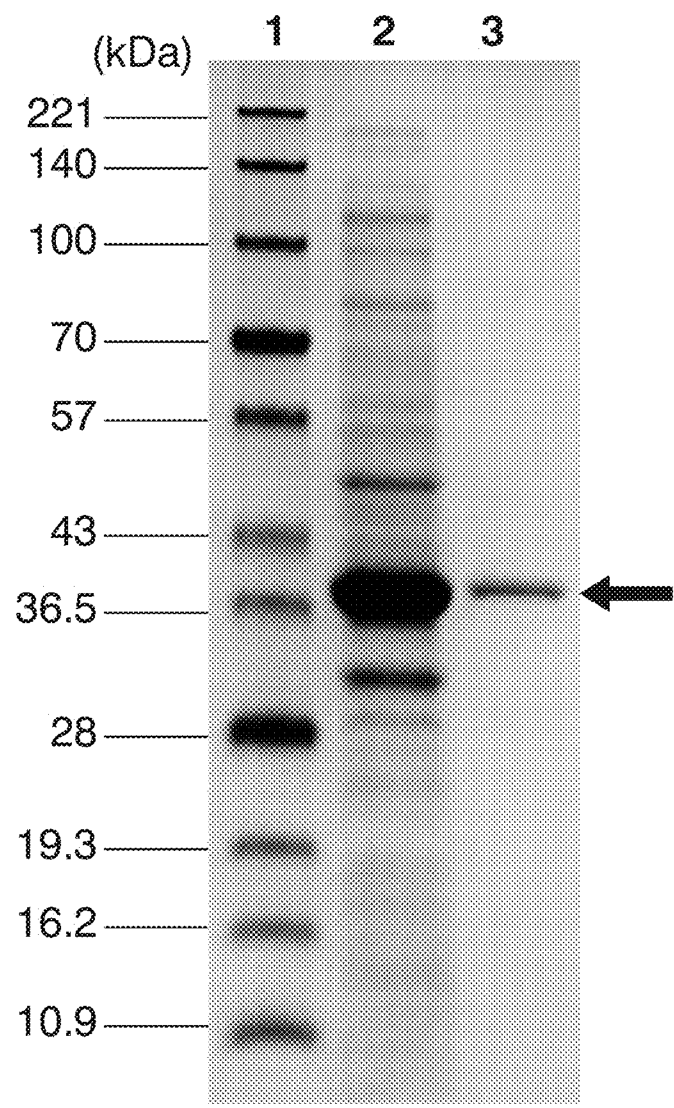
FIG. 2 is a diagram showing the SDS-PAGE analysis result of the AR19M-177-21 protein obtained by expressing the AR19M-177-21 gene in *E. coli* in Example 1.

Many microorganisms including filamentous fungi, bacteria and Archaea are difficult to culture, and it is said that 99% of the microorganisms inhabiting microbial environments such as soil are still unknown. In particular, the culturing of microorganisms that exist in high-temperature environments is extremely difficult, and it is thought that only a mere 0.1% or less of the microorganisms that exist in soils have been able to be isolated and cultured with currently available microbial culturing techniques. This difficulty in culturing microorganisms from high-temperature soils is one of the reasons hindering the development of thermostable enzymes.

In recent years, as a result of the development of next generation giga sequencers that enable a large amount of sequencing of giga base pairs, whole genome sequencing of the microbial flora contained in soils or the like has become possible. By using this analysis technology, the metagenomic analysis method has been proposed, in which the genomic DNA of a microbial group is prepared from an environmental sample such as soil, the genomes of the group having non-uniform and miscellaneous genomic compositions are sequenced directly and comprehensively, and the sequenced data are assembled by a parallel computer, thereby reconstructing the genomic sequences of the microbial flora. This method has contributed to rapid progress in the genome sequencing of microorganisms that are difficult to culture.

As shown in Example 1 described below, the inventors of the present invention extracted the genomic DNA (metagenomic DNA) of microbial groups from collected high-temperature hot spring soils (for example, hot spring water of 58 to 78° C. containing soil, mud, biomat and biofilm and the like), and conducted shotgun sequencing and annotation of the metagenomic DNA, thus obtaining open reading frames (ORFs) encoding amino acid sequences similar to known xylanase enzymes (for example, amino acid sequences having 20% or higher sequence identity, and an expectation value (E-value) of less than $1e^{-20}$). For each of the 33 ORFs for which a xylanase catalytic domain was confirmed, a primer was designed based on the nucleotide sequence information of the ORF, and gene candidates were cloned from the metagenomic DNA of the high-temperature hot spring soils by the PCR method. The PCR-cloned DNAs were incorporated into *E. coli*, and proteins encoded by these nucleotide sequences were expressed, and subjected to functional screening by xylan degradation activity assay. Finally, a thermostable xylanase (hereafter also referred to as "AR19M-177-21") having xylanase activity was obtained from these ORFs. The amino acid sequence and nucleotide sequence of AR19M-177-21 are represented by SEQ ID NO: 1 and SEQ ID NO: 2 respectively.

As shown below in Example 1 <9>, AR19M-177-21 exhibits high hydrolysis activity against xylan, but exhibits almost no degradation activity against phosphoric acid swollen Avicel (hereafter often abbreviated as PSA), the crystalline cellulose Avicel, carboxymethyl cellulose (hereafter often abbreviated as CMC), lichenan composed of β-1,3- and β-1,4-linked glucan, laminarin composed of β-1,3- and β-1,6-linked glucan, p-nitrophenyl-β-D-xylopyranoside (hereafter often abbreviated as PNPX), and p-nitrophenyl-β-D-glucopyranoside (hereafter often abbreviated as PNPG).

In the present description, the expression "xylanase activity" means an activity that causes the hydrolysis of xylan (xylan hydrolysis activity) when xylan is used as the substrate.

Further, in the present description, the expression "has activity" means that the enzyme acts against at least one substrate, with a significant difference occurring in the amount of reducing ends or the color development reaction of the hydrolyzed substrate compared with a negative control. Accordingly, the expression "has xylanase activity" means that the enzyme acts at least against xylan, and generates a significant difference in the amount of reducing ends or the color development reaction of the hydrolyzed substrate compared with a negative control.

Further, in a separate aspect, the expression "has xylanase activity" means that, under conditions of pH 6.0, and within a temperature range of 40 to 95° C., the enzyme has a hydrolysis activity of at least 30 U/mg protein, at least against xylan.

Furthermore, in yet another aspect, the expression "has xylanase activity" means that, under conditions of 85° C., and within a pH range of 5.0 to 8.0, the enzyme has a hydrolysis activity of at least 50 U/mg protein, at least against xylan.

When the amino acid sequence of AR19M-177-21 was searched against a database of known amino acid sequences, the amino acid sequence that showed the highest sequence identity was that of an endo-1,4-β-xylanase (Genbank: ACB09229.1) (Genbank: AEY92972.1) (SEQ ID NO: 6) belonging to the GH10 family of the bacterium *Thermotoga* sp. RQ2 of the phylum Thermotogae, and the sequence identity (homology) was 63% for the entire length, and 75% for the xylanase catalytic domain. From the substrate specificity and the sequence identity of the amino acid sequence with that of a known protein, it is clear that AR19M-177-21 is a novel xylanase belonging to the GH10 family.

AR19M-177-21 has xylanase activity at least under conditions of 85° C. and pH 6.0. Actually, as shown below in Example 1 <10>, under conditions of pH 6.0, AR19M-177-21 exhibits xylanase activity within a temperature range from 40 to 95° C., and exhibits particularly strong xylanase activity in a temperature range from 80 to 90° C. More specifically, under conditions of pH 6.0, the xylanase activity of AR19M-177-21 increases with increasing temperature within a range from 40 to 85° C., but then decreases rapidly above 95° C.

Generally, in a protein having some form of bioactivity, one or a plurality of amino acids can be deleted, substituted, or added, without impairing the bioactivity. In other words, in AR19M-177-21, one or a plurality of amino acids can be deleted, substituted, or added without impairing the glycoside hydrolysis activity including the xylanase activity.

Hence, the thermostable xylanase according to the present invention is a thermostable glycoside hydrolase having a xylanase catalytic domain including any of the following (A) to (C):

(A) a polypeptide including the amino acid sequence represented by SEQ ID NO: 1 (namely, AR19M-177-21), (B) a polypeptide including an amino acid sequence in which at least one amino acid has been deleted, substituted, or added in the amino acid sequence represented by SEQ ID NO: 1, and having xylanase activity at least under conditions of 85° C. and pH 6.0, or (C) a polypeptide including an amino acid sequence having 80% or greater sequence identity with the amino acid sequence represented by SEQ ID NO: 1, and having xylanase activity at least under conditions of 85° C. and pH 6.0.

In the present description, a "polypeptide in which an amino acid is deleted" means a polypeptide in which a portion of the amino acids which constitute the polypeptide is missing (removed).

In the present description, a "polypeptide in which an amino acid is substituted" means a polypeptide in which an amino acid which constitutes the polypeptide has been replaced with a different amino acid.

In the present description, a "polypeptide in which an amino acid is added" means a polypeptide in which a new amino acid has been inserted within the polypeptide.

In the aforementioned polypeptide of (B), the number of amino acids deleted, substituted, or added in the amino acid sequence represented by SEQ ID NO: 1 is preferably 1 to 20, more preferably 1 to 10, and still more preferably 1 to 5.

In the aforementioned polypeptide of (C), the sequence identity with the amino acid sequence represented by SEQ ID NO: 1 is not specifically limited as long as it is 80% or greater but less than 100%, but the sequence identity is preferably 85% or greater but less than 100%, more preferably 90% or greater but less than 100%, still more preferably 95% or greater but less than 100%, and most preferably 98% or greater but less than 100%.

The sequence identity (homology) between a pair of amino acid sequences is determined by juxtaposing the two amino acid sequences, while inserting gaps in some parts of the sequences to account for insertions and deletions, so as to achieve the best match between corresponding amino acids, and then calculating the proportion of matched amino acids relative to the whole amino acid sequences, excluding gaps, in the resulting alignment. The sequence identity between a pair of amino acid sequences can be determined using a variety of homology search software well known in the art. The sequence identity value between amino acid sequences in the present invention is obtained by calculation on the basis of an alignment obtained from the publicly known homology search software BLASTP.

The aforementioned polypeptides of (B) and (C) may be artificially designed, or may be homologs of AR19M-177-21 or the like, or partial proteins thereof.

Each of the aforementioned polypeptides of (A) to (C) may be chemically synthesized based on the amino acid sequence, or may be generated by a protein expression system using the polynucleotide according to the present invention described below. Further, each of the polypeptides of (B) and (C) can also be artificially synthesized based on the polypeptide including the amino acid sequence represented by SEQ ID NO: 1, by using a gene recombination technique to introduce amino acid mutation(s).

Each of the polypeptides of (A) to (C) has xylanase activity at least under conditions of 85° C. and pH 6.0. As a result, a thermostable xylanase can be obtained by having any of the polypeptides of (A) to (C) as the xylanase catalytic domain.

The thermostable xylanase according to the present invention uses at least xylan as a substrate. The thermostable xylanase may also use other β-glucans besides xylan as a substrate. Examples of substrates besides xylan that can act as substrates for the thermostable xylanase according to the present invention include PNPX, PNPG, p-nitrophenyl-α-L-arabinofuranoside, p-nitrophenyl-α-L-arabinopyranoside, p-nitrophenyl-β-L-arabinopyranoside, p-nitrophenyl-β-D-mannopyranoside, p-nitrophenyl-α-D-galactopyranoside, p-nitrophenyl-β-D-galactopyranoside, glucans composed of β-1,3 and β-1,4 linkages such as lichenan, crystalline celluloses such as Avicel, crystalline bacterial cellulose (bacterial microcrystalline cellulose, BMCC) and filter paper, the non-crystalline cellulose known as phosphoric acid swollen Avicel (hereafter often abbreviated as PSA), CMC, glucans composed of β-1,4 linkages, oligosaccharides composed of β-1,4 linkages such as cellobiose, glucans composed of β-1,3 and β-1,6 linkages such as laminarin, glucans composed of β-1,3 linkages, glucans composed of β-1,6 linkages, and oligosaccharides composed of β-1,6 linkages such as gentiobiose.

The thermostable xylanase according to the present invention exhibits xylanase activity at least under conditions of pH 6.0, and preferably within a temperature range from 80 to 90° C., more preferably within a temperature range from 70 to 90° C., still more preferably within a temperature range from 60 to 90° C., still more preferably within a temperature range from 50 to 95° C., and most preferably within a temperature range from 40 to 95° C. The optimum temperature of the thermostable xylanase according to the present invention is preferably within a range from 75 to 95° C., and more preferably within a range from 80 to 90° C.

The optimum pH of the thermostable xylanase according to the present invention varies depending on the reaction temperature, but falls within a range from pH 5.0 to 7.0. The thermostable xylanase according to the present invention preferably exhibits xylanase activity at least within a range from pH 5.0 to 8.0.

The thermostable xylanase according to the present invention may also have other glycoside hydrolase activity besides the xylanase activity. Examples of this other glycoside hydrolase activity include endoglucanase activity, β-xylosidase activity, β-glucosidase activity and cellobiohydrolase activity.

The thermostable xylanase according to the present invention may be an enzyme composed solely of the xylanase catalytic domain including any of the aforementioned polypeptides of (A) to (C), or may also include other domains. Examples of these other domains include other domains of conventionally known xylanases besides the xylanase catalytic domain. For example, the thermostable xylanase according to the present invention also includes enzymes obtained by substituting a xylanase catalytic domain in a publicly known xylanase with any of the aforementioned polypeptides of (A) to (C).

The thermostable xylanase according to the present invention may also have, at either the N-terminal or the C-terminal, a signal peptide capable of migration to and localization within a specific region within a cell, or a signal peptide that causes secretion from a cell. Examples of these signal peptides include an apoplastic transport signal peptide, an endoplasmic reticulum retention signal peptide, a nuclear transport signal peptide, or a secretory signal peptide. Specific examples of the endoplasmic reticulum retention signal peptide include signal peptides including an HDEL amino acid sequence. In those cases when the thermostable xylanase according to the present invention has a signal peptide at the N-terminal or the C-terminal, the thermostable xylanase expressed in a transformant can be secreted from the cell or localized within the endoplasmic reticulum or the like of the cells.

Furthermore, the thermostable xylanase according to the present invention may also have various types of tags added, for example at the N-terminal or the C-terminal of the thermostable xylanase, so as to facilitate easy purification in the case of generation using an expression system. Examples of tags that may be used include the types of tags widely used in the expression or purification of recombinant proteins, such as an His tag, an HA (hemagglutinin) tag, an Myc tag and a Flag tag.

[Polynucleotide Encoding Thermostable Xylanase]

The polynucleotide according to the present invention encodes the thermostable xylanase according to the present invention. The thermostable xylanase can be generated by using the expression system of a host made by introducing an expression vector incorporating the polynucleotide into the host.

Specifically, the polynucleotide according to the present invention is a polynucleotide having a region encoding a xylanase catalytic domain, the region including any of the following nucleotide sequences (a) to (e):

(a) a nucleotide sequence encoding a polypeptide including the amino acid sequence represented by SEQ ID NO: 1, (b) a nucleotide sequence encoding a polypeptide which includes an amino acid sequence in which at least one amino acid has been deleted, substituted, or added in the amino acid sequence represented by SEQ ID NO: 1, and has xylanase activity at least under conditions of 85° C. and pH 6.0, (c) a nucleotide sequence encoding a polypeptide which includes an amino acid sequence having 80% or greater sequence identity with the amino acid sequence represented by SEQ ID NO: 1, and has xylanase activity at least under conditions of 85° C. and pH 6.0, (d) a nucleotide sequence, having 80% or greater sequence identity with a nucleotide sequence represented by SEQ ID NO: 2, and encoding a polypeptide that has xylanase activity at least under conditions of 85° C. and pH 6.0, or (e) a nucleotide sequence of a polynucleotide which hybridizes with a polynucleotide including the nucleotide sequence represented by SEQ ID NO: 2 under stringent conditions, the nucleotide sequence encoding a polypeptide having xylanase activity at least under conditions of 85° C. and pH 6.0.

In the present description, a "polynucleotide in which a nucleotide is deleted" means a polynucleotide in which a portion of the nucleotides which constitute the polynucleotide is missing (removed).

In the present description, a "polynucleotide in which a nucleotide is substituted" means a polynucleotide in which a nucleotide which constitutes the polynucleotide has been replaced with a different nucleotide.

In the present description, a "polynucleotide in which a nucleotide is added" means a polynucleotide in which a new nucleotide has been inserted within the polynucleotide.

In the present description, the expression "stringent conditions" can be exemplified by the method disclosed in Molecular Cloning: A Laboratory Manual, Third Edition (Sambrook et al., Cold Spring Harbor Laboratory Press). This example includes conditions in which hybridization is performed by incubation in a hybridization buffer composed of 6×SSC (composition of 20×SSC: 3 M sodium chloride, 0.3 M citric acid solution, pH 7.0), 5×Denhardt's solution (composition of 100×Denhardt's solution: 2% by mass of bovine serum albumin, 2% by mass of Ficoll, 2% by mass of polyvinylpyrrolidone), 0.5% by mass of SDS, 0.1 mg/mL of salmon sperm DNA, and 50% formamide, at a temperature of 42 to 70° C. for several hours to overnight. The washing buffer used in the washing performed after the incubation is preferably 1×SSC solution containing 0.1% by mass of SDS, and is more preferably 0.1×SSC solution containing 0.1% by mass of SDS.

In the aforementioned nucleotide sequences of (a) to (e), it is preferable to select a degenerate codon having a high frequency of usage in the host. For example, the aforementioned nucleotide sequence of (a) may be either the nucleotide sequence represented by SEQ ID NO: 2, or a nucleotide sequence obtained by modifying the nucleotide sequence represented by SEQ ID NO: 2 to codons having a higher frequency of usage in the host without changing the amino acid sequence encoded by the nucleotide sequence. This modification of codons can be achieved using a known gene sequence variation technique or artificial gene synthesis.

The polynucleotide including the nucleotide sequence represented by SEQ ID NO: 2 may be chemically synthesized based on the nucleotide sequence information, or may be obtained from the natural world by using gene recombination techniques as either a full length gene that encodes AR19M-177-21 (also referred to as the "AR19M-177-21 gene" or the "gene clone AR19M-177-21") or a partial region thereof including the xylanase catalytic domain (a region encoding the partial region including the 314 amino acid residues from the threonine (T) at position 31 through to the leucine (L) at position 344 in SEQ ID NO: 1). The full length of the AR19M-177-21 gene or the partial region thereof can be obtained, for example, by collecting a sample containing microorganisms from the natural world, and conducting PCR using a genomic DNA recovered from the sample as a template, with a forward primer and a reverse primer designed by normal methods based on the nucleotide sequence represented by SEQ ID NO: 2. The cDNA synthesized by a reverse transcription reaction using mRNA recovered from the sample as a template may also be used as a template. The sample from which the nucleic acid for use as a template is recovered is preferably a sample collected from a high-temperature environment such as hot spring soil.

In the aforementioned nucleotide sequence of (d), the sequence identity with the nucleotide sequence represented by SEQ ID NO: 2 is not specifically limited as long as it is 80% or greater but less than 100%, but the sequence identity is preferably 85% or greater but less than 100%, more preferably 90% or greater but less than 100%, still more preferably 95% or greater but less than 100%, and most preferably 98% or greater but less than 100%.

The sequence identity (homology) between a pair of nucleotide sequences is determined by juxtaposing the two nucleotide sequences, while inserting gaps in some parts of the sequences to account for insertions and deletions, so as to achieve the best match between corresponding nucleotides, and then calculating the proportion of matched nucleotides relative to the whole nucleotide sequences, excluding gaps, in the resulting alignment. The sequence identity between a pair of nucleotide sequences can be determined using a variety of homology search software well known in the art. The sequence identity value between nucleotide sequences in the present invention is obtained by calculation on the basis of an alignment obtained from the publicly known homology search software BLASTN.

For example, each of the polynucleotides including the aforementioned nucleotide sequence of (b), (c) or (d) can be artificially synthesized by deleting, substituting, or adding one or a plurality of nucleotides in a polynucleotide including the nucleotide sequence represented by SEQ ID NO: 2. Further, the nucleotide sequence of (b), (c) or (d) may also be a full length sequence of a homologous gene of the AR19M-177-21 gene or a partial sequence thereof. The homologous gene of the AR19M-177-21 gene can be obtained by a gene recombination technique used in obtaining homologous genes of a gene for which the nucleotide sequence is already known.

The polynucleotide according to the present invention may have only the region encoding the xylanase catalytic domain, or may also have, in addition to this region, one or more other regions encoding a cellulose-binding module, a linker sequence, various types of signal peptides, or various types of tags or the like.

[Expression Vector]

The expression vector according to the present invention incorporates the aforementioned polynucleotide according to the present invention, and is capable of expressing, in a host cell, a polypeptide having xylanase activity at least under conditions of 85° C. and pH 6.0. In other words, the expression vector of the present invention is an expression vector into which the polynucleotide according to the present invention has been incorporated in a state capable of expressing the thermostable xylanase according to the present invention. More specifically, it is necessary that an expression cassette, composed, in order from the upstream side, of DNA having a promoter sequence, the aforementioned polynucleotide according to the present invention and DNA having a terminator sequence, is incorporated into the expression vector. Incorporation of the polynucleotide into an expression vector can be achieved using known gene recombination techniques. A commercially available expression vector preparation kit may also be used to achieve incorporation of the polynucleotide into the expression vector.

In the present description, an "expression vector" is a vector including, in order from the upstream side, DNA having a promoter sequence, DNA having a sequence for incorporating foreign DNA, and DNA having a terminator sequence.

The aforementioned expression vector may be a vector for introduction into a prokaryotic cell such as *E. coli*, or a vector for introduction into a eukaryotic cell such as a yeast, a filamentous fungus, an insect cultured cell, a mammalian cultured cell, or a plant cell. Any arbitrary widely used expression vector can be selected and used in accordance with the respective host.

The expression vector according to the present invention is preferably an expression vector into which not only the aforementioned polynucleotide according to the present invention, but also a drug resistance gene or the like, has been incorporated. This facilitates the screening of host cells transformed by the expression vector and non-transformed host cells.

Examples of the drug resistance gene include a kanamycin resistance gene, a hygromycin resistance gene and a bialaphos resistance gene.

[Transformant]

The transformant according to the present invention is a transformant into which the expression vector according to the present invention has been introduced. In this transformant, the aforementioned thermostable xylanase according to the present invention can be expressed. The host into which the expression vector is introduced may be a prokaryotic cell such as *E. coli*, or a eukaryotic cell such as a yeast, a filamentous fungus, an insect cultured cell, a mammalian cultured cell, or a plant cell. In other words, examples of the transformant according to the present invention include *E. coli*, a yeast, a filamentous fungus, an insect cultured cell, a mammalian cultured cell or a plant cell into which the expression vector according to the present invention has been introduced.

By culturing a transformant of *E. coli*, the thermostable xylanase according to the present invention can be generated more easily and in large amounts. On the other hand, because proteins are glycosylated in eukaryotic cells, by using a transformant of a eukaryotic cell, a thermostable xylanase can be generated which exhibits superior thermostability to that achieved by using a transformant of a prokaryotic cell.

There are no particular limitations on the method used for producing the transformant using the expression vector, and the types of methods typically used in the production of transformants can be employed. Examples of methods that can be used include an *Agrobacterium* method, a particle gun method, an electroporation method, and a PEG (polyethylene glycol) method. Of these, if the host is a plant cell, a particle gun method or an *Agrobacterium* method is preferred.

When a prokaryotic cell, a yeast, a filamentous fungus, an insect cultured cell, or a mammalian cultured cell or the like is used as the host, the obtained transformant can generally be cultured by a conventional method in a similar manner to that of the non-transformed host.

[Method for Producing Thermostable Xylanase]

The method for producing a thermostable xylanase according to the present invention is a method for generating a thermostable xylanase in the aforementioned transformant according to the present invention. By culturing a transformant that has been produced using an expression vector into which the aforementioned polynucleotide according to the present invention has been incorporated downstream from a promoter having no ability to regulate the timing or the like of the expression, the thermostable xylanase according to the present invention is expressed constitutively within the transformant. On the other hand, in the case of a transformant produced using a so-called expression inducible promoter to induce the expression by means of a specific compound or temperature condition or the like, the thermostable xylanase is expressed in the transformant by culturing the transformant and conducting an induction treatment suitable for the respective expression-inducing condition.

The thermostable xylanase generated by the transformant may be used in a state where it is retained inside the transformant, or may be extracted from the transformant and purified.

The method used for extracting and purifying the thermostable xylanase from the transformant is not particularly limited, as long as the method does not impair the activity of the thermostable xylanase, and extraction can be carried out by methods commonly used for extracting polypeptides from cells or biological tissue. Examples of the method include a method in which the transformant is immersed in an appropriate extraction buffer to extract the thermostable xylanase, and the resulting liquid extract and the solid residue are then separated. The extraction buffer preferably contains a solubilizing agent such as a surfactant. If the transformant is a plant, then the transformant may be shredded or crushed prior to immersion in the extraction buffer.

Further, in terms of the method used for separating the liquid extract and the solid residue, known solid-liquid separation treatments such as a filtration method, pressurized filtration method or centrifugation treatment may be used, or the extraction buffer containing the immersed transformant may be squeezed. The thermostable xylanase in the liquid extract can be purified by known purification methods such as a salting-out method, ultrafiltration method, or chromatography method.

If the thermostable xylanase according to the present invention is expressed in a state having a secretory signal peptide in the transformant, then a solution containing the thermostable xylanase can be readily obtained by culturing the transformant and then collecting the culture liquid supernatant obtained by removal of the transformant from the obtained culture. Further, if the thermostable xylanase according to the present invention has a tag such as an His tag, then the thermostable xylanase in the liquid extract or in the culture supernatant can be easily purified by an affinity chromatography method using the tag.

In other words, the method for producing a thermostable xylanase according to the present invention includes culturing the transformant according to the present invention, generating the thermostable xylanase within the transformant, and, according to need, extracting the thermostable xylanase from the transformant and purifying the thermostable xylanase.

[Glycoside Hydrolase Mixture]

The glycoside hydrolase mixture according to the present invention includes the aforementioned thermostable xylanase according to the present invention or a thermostable xylanase produced by the method for producing a thermostable xylanase according to the present invention, and at least one other glycoside hydrolase. The thermostable xylanase produced by the aforementioned method for producing a thermostable xylanase according to the present invention may be in a state where it is retained inside the transformant, or may be extracted from the transformant and purified. By using the thermostable xylanase according to the present invention as a mixture with one or more other glycoside hydrolases in a polysaccharide hydrolysis reaction, persistent lignocellulose can be degraded more efficiently.

There are no particular limitations on the other glycoside hydrolase besides the aforementioned thermostable xylanase included in the glycoside hydrolase mixture, as long as it exhibits lignocellulose hydrolysis activity. Examples of the other glycoside hydrolase besides the aforementioned thermostable xylanase included in the glycoside hydrolase mixture include hemicellulases such as β-xylosidases, as well as cellobiohydrolases, β-glucosidases and endoglucanases. The glycoside hydrolase mixture according to the present invention is preferably a mixture containing at least one of a hemicellulase and an endoglucanase in addition to the aforementioned thermostable xylanase, and is more preferably a mixture containing both a hemicellulase and an endoglucanase in addition to the aforementioned thermostable xylanase. Among the various possibilities, the glycoside hydrolase mixture according to the present invention is preferably a mixture containing at least one glycoside hydrolase selected from the group consisting of xylanases, β-xylosidases, cellobiohydrolases and endoglucanases in addition to the aforementioned thermostable xylanase, and is more preferably a mixture containing all of a xylanase, a β-xylosidase, a cellobiohydrolase and an endoglucanase in addition to the thermostable xylanase.

The other glycoside hydrolase included in the glycoside hydrolase mixture is preferably a thermostable glycoside hydrolase having glycoside hydrolase activity at least at 85° C., and is more preferably a thermostable glycoside hydrolase having glycoside hydrolase activity at 70 to 90° C. By ensuring that all of the enzymes contained in the glycoside hydrolase mixture are thermostable (that is, have an optimum temperature for the enzymatic activity or a thermal denaturation temperature for the enzyme protein of 70° C. or higher), the lignocellulose degradation reaction by the glycoside hydrolase mixture can be conducted efficiently under high-temperature conditions. In other words, if the glycoside hydrolase mixture contains only thermostable glycoside hydrolases, then by using the glycoside hydrolase mixture in a lignocellulose hydrolysis treatment, it becomes possible to conduct the lignocellulose hydrolysis reaction in a high-temperature environment in which the hydrolysis temperature is from 70 to 90° C. With this high-temperature hydrolysis, the amount of enzymes and the time required for the hydrolysis can be reduced markedly, and the hydrolysis costs can be cut dramatically.

[Method for Producing Lignocellulose Degradation Product]

The method for producing a lignocellulose degradation product according to the present invention is a method for obtaining a lignocellulose degradation product containing a hemicellulose degradation product by hydrolyzing a lignocellulose-containing material containing hemicellulose, and more specifically hemicellulose including xylan, with the thermostable xylanase according to the present invention.

Specifically, the lignocellulose degradation product containing a hemicellulose degradation product is generated by bringing a lignocellulose-containing material containing hemicellulose, and more specifically hemicellulose including xylan, into contact with the thermostable xylanase according to the present invention, the transformant according to the present invention, a thermostable xylanase produced by the method for producing a thermostable xylanase according to the present invention, or the glycoside hydrolase mixture according to the present invention.

As lignocellulose degradation product containing a hemicellulose degradation product, for example, xylose, xylooligosaccharide and the like can be mentioned.

There are no particular limitations on the lignocellulose-containing material containing hemicellulose, and more specifically hemicellulose including xylan, provided the material contains hemicellulose, and more specifically hemicellulose that contains xylan. Specific examples of such materials include biomass such as weeds and agricultural waste materials, or used paper or the like. The material is preferably subjected to a mechanical treatment such as crushing or shredding, a chemical treatment with acid or alkali or the like, or a treatment such as immersion or dissolution in an appropriate buffer, prior to being brought into contact with the thermostable xylanase according to the present invention.

The reaction conditions for the hydrolysis reaction of the hemicellulose, and more specifically xylan, by the thermostable xylanase according to the present invention may be any conditions under which the thermostable xylanase exhibits xylanase activity. For example, the reaction is preferably conducted at a temperature of 60 to 90° C. and a pH of 5.0 to 8.0, more preferably conducted at a temperature of 70 to 90° C. and a pH of 5.0 to 7.0, and still more preferably conducted at a temperature of 80 to 90° C. and a pH of 5.0 to 7.0. The reaction time for the hydrolysis reaction may be adjusted appropriately with due consideration of the type, the method of pretreatment, and the amount and the like of the hemicellulose, or more specifically the lignocellulose-containing material containing hemicellulose including xylan, that is supplied to the hydrolysis reaction. For example, the hydrolysis reaction may be performed for a reaction time of 10 minutes to 100 hours, but in the case of degradation of a cellulosic biomass, the hydrolysis reaction time is preferably from 1 to 100 hours.

In the lignocellulose hydrolysis reaction, it is also preferable to use at least one other type of glycoside hydrolase in addition to the thermostable xylanase according to the present invention, with the enzymes used either simultaneously or separately. This other glycoside hydrolase may be similar to the glycoside hydrolases mentioned above for inclusion in the aforementioned glycoside hydrolase mixture, and is preferably a thermostable glycoside hydrolase having glycoside hydrolase activity at least at 85° C., and preferably at least at temperatures of 70 to 90° C. Further, one aspect of the aforementioned method for producing a lignocellulose degradation product uses the thermostable xylanase according to the present invention, the transformant according to the present invention, or a thermostable xylanase produced by the method for producing a thermostable xylanase according to the present invention, whereas another aspect of the method uses the aforementioned glycoside hydrolase mixture.

EXAMPLES

Next, the present invention is described in further detail based on a series of Examples, but the present invention is in no way limited by the following Examples.

[Example 1] Cloning of Novel Thermostable Xylanase from Hot Spring Soil

<1> DNA Extraction from Hot Spring Soil and Whole Genome Sequencing (WGS)

With the purpose of searching for genes of novel thermostable xylanases which exhibit activity at 70 to 90° C., soil DNA was collected from neutral to weakly alkaline hot springs, and nucleotide sequencing was conducted of the metagenomic DNA of the microbial flora contained in the soils.

The soil samples from neutral to weakly alkaline hot springs were obtained by collecting hot spring water containing soil, clay and biomat from five sampling points (metagenomic DNA samples N2, AR19, AR15, OJ1 and H1) at 3 locations in Japan having gushing high-temperature outdoor hot springs. These hot spring soil samples each had a temperature within a range from 58 to 78° C. and a pH within a range from 7.2 to 8 at the time of collection.

DNA was extracted from 10 g of each of the collected hot spring soil samples by using a DNA extraction kit (ISOIL Large for Beads ver.2, manufactured by NIPPON GENE Co., Ltd.). The extracted DNA was subjected to shotgun sequencing of the metagenomic DNA using a GS FLX Titanium 454 manufactured by Roche Diagnostics Ltd., and a HiSeq 2000 manufactured by Illumina, Inc. Five μg of the extracted DNA was used in the 454 sequencer, whereas in the HiSeq 2000 sequencer, an amplified product prepared using a genome DNA amplification kit (GenomiPhi V2 DNA Amplification Kit, manufactured by GE Healthcare, Inc.) was used to perform the metagenomic DNA sequencing.

In the case of sequencing using the HiSeq 2000, the DNA library and the reagent were introduced into the flow cell using a cBot manufactured by Illumina, Inc., and from a single DNA molecule, a cluster having the same sequence was formed automatically within the flow cell. Using the HiSeq 2000, 101 bp paired end sequencing was performed, thus obtaining the metagenomic sequence data.

Metagenomic DNA sequencing of the hot spring soil sample AR19 in the 454 sequencer yielded an average read length of 396 bp, a total read number of 2,766,332, and a total quantity of sequenced genomes of 1,106,243,280 bp, and sequencing in the HiSeq 2000 sequencer yielded an average read length of 92.65 bp paired ends, a total read number of 894,238,096, and a total quantity of sequenced genomes of 83,112,168,755 bp, meaning a whole genome sequence (WGS) data set totaling 84.2 Gbp was obtained.

<2> Assembly and Statistics of Hot Spring Metagenomic Data

For the nucleotide sequences read by the 454 sequencer and the HiSeq 2000 sequencer, CLC Genomics Workbench (ver. 5.5.1) from CLC bio A/S was used to perform quality filtering and de novo assembly. Following quality filtering, the total read length of the reads obtained from the 454 sequencer was 1,084,400,576 bp, and the total read length of the nucleotide sequence data obtained from the HiSeq 2000 sequencer was 81,323,692,563 bp. Following assembly, the number of contigs having a length of 500 bp or longer was 967,925, the total length was 419,787,603 bp, and the maximum contig length was 287,641 bp.

<3> Prediction of Open Reading Frames (ORFs) of Xylanase

Sequences having EC numbers of 3.2.1.4 (cellulase), 3.2.1.21 (β-glucosidase), 3.2.1.37 (β-xylosidase), 3.2.1.91 (cellulose 1,4-β-cellobiosidase) and 3.2.1.8 (endo-1,4-β-xylanase) were downloaded (date of access: Dec. 9, 2011) from the UniProt database (http://www.uniprot.org/), and a proteome local database of these glycoside hydrolase genes was constructed. Using the annotation software Metagene (Noguchi et al., DNA Research, 2008, 15(6)), gene regions (=open reading frames) were predicted from the contig sequences obtained in section <2> above (Metagene option: -m). In order to extract the glycoside hydrolase gene from the predicted ORFs, reference was made to the local database using BLASTP (blastall ver. 2.2.18). The optional conditions for BLASTP were set such that: "Filter query sequence=false", "Expectation value (E)<$1e^{-20}$" (hereafter, default values were set such that: "Cost to open a gap=−1", "Cost to extended gap=−1", "X dropoff value for gapped alignment=0", "Threshold for extending hits=0", and "Word size=default"), and the hit ORF sequences were collected as glycoside hydrolase genes. The collected nucleotide sequences included nucleotide sequences of various glycoside hydrolase genes such as cellulases, endohemicellulases and debranching enzymes.

<4> Glycoside Hydrolase (GH) Family Classification of Genes

Functional classification of the nucleotide sequences collected in section <3> above was performed with reference to the protein functional domain sequence database Pfam HMMs (Pfam version 23.0 and HMMER v2.3; Finn et al., Nucleic Acids Research Database, 2010, Issue 38, pp. D211-222). Specifically, the glycoside hydrolase (GH) family of each of the nucleotide sequences collected in section <3> above was determined on the basis of homology with the Pfam domain database by using the protein motif search program HMMER (Durbin et al., "The theory behind profile HMMs. Biological sequence analysis: probabilistic models of proteins and nucleic acids", 1998, Cambridge University Press; hmmpfam (Ver. 2.3.2), E-value cutoff<$1e^{-5}$; Database=Pfam_fs (models that can be used to find fragments of the represented domains in a sequence)). Nucleotide sequences which covered 70% or more of the GH catalytic domain sequence were counted as enzyme genes belonging to that particular family.

Based on the BLASTP homology search and HMMER using the metagenome AR19 sequence data, 33 ORFs (29 full-length ORFs and 4 partial length ORFs) were predicted as xylanase genes. The GH family classifications of these ORFs are shown in Table 1. As shown in Table 1, 17 full-length ORFs of xylanase genes belonging to the GH family 10, 7 full-length ORFs of xylanase genes belonging to the GH family 11, and 4 full-length ORFs of xylanase genes belonging to the GH family 43 were obtained from the metagenome AR19. Primers were designed for all of the ORFs that were predicted as xylanases, and these genes were cloned from the hot spring soil metagenomic DNA by PCR. As a result, a xylanase gene was isolated from the open reading frame AR19M-177 belonging to the GH family 10 and having a xylanase gene nucleotide sequence.

TABLE 1

| | GH family classification of xylanase genes | | | | |
|---|---|---|---|---|---|
| AR19 Metagenome | GH10 | GH11 | GH43 | Other GH families | Total |
| full-length ORFs | 17 | 7 | 4 | 1 | 29 |
| partial length ORFs | 2 | 0 | 1 | 1 | 4 |
| Total number of ORFs | 19 | 7 | 5 | 2 | 33 |

<5> Open Reading Frame AR19M-177

The open reading frame AR19M-177 encoded a polypeptide (SEQ ID NO: 1) including 355 amino acid residues and was a full-length sequence (SEQ ID NO: 2), such that the polypeptide started from methionine which was an amino acid residue at position 1, and the 3' end of the nucleotide sequence encoding the polypeptide ended with a termination codon. According to analysis using the signal sequence prediction software SignalP 4.1, the 29 amino acid residues from the methionine (M) at position 1 through to the glycine (G) at position 29 function as a secretion signal in the polypeptide encoded by the open reading frame AR19M-177. Further, based on the sequence homology of the motif, it was presumed that the 314 amino acid residues from the threonine (T) at position 31 through to the leucine (L) at position 344 in the polypeptide encoded by the open reading frame AR19M-177 encoded the catalytic domain of glycoside hydrolase family 10. This ORF was a novel sequence that exhibited 69% and 75% amino acid sequence identity respectively with the full length and the GH10 catalytic domain of the endo-1,4-β-xylanase (Genbank: ACB09229.1) belonging to the GH10 family of the bacterium Thermotoga sp. RQ2 of the phylum Thermotogae. Both sequence homology values were calculated using the ClustalW algorithm.

<6> Gene Cloning

Using a forward primer composed of the nucleotide sequence represented by SEQ ID NO: 5 (5'-CACCATGGGGGTGAAGAGCGTGAAA-3': 4 nucleotides (CACC) were added to the 5'-end of the nucleotide sequence represented by SEQ ID NO: 3, wherein the CACC added to the 5' side is a sequence to enable insertion into a vector), and a reverse primer composed of the nucleotide sequence represented by SEQ ID NO: 4 (5'-TCATTTACCCTTCAGCTTTTC-3'), PCR was performed using the hot spring soil DNA that had been amplified by the genome DNA amplification kit (GenomiPhi V2 DNA Amplification Kit, manufactured by GE Healthcare, Inc.) as a template. The nucleotide sequence represented by SEQ ID NO: 3 is homologous (identical) with the partial sequence composed of the nucleotides from positions 1 to 21 of the nucleotide sequence represented by SEQ ID NO: 2. Further, the nucleotide sequence represented by SEQ ID NO: 4 is complementary with the partial sequence composed of the nucleotides from positions 1,048 to 1,068 of the nucleotide sequence represented by SEQ ID NO: 2. The amplified PCR product was inserted into a pET101/D-TOPO vector of a Champion pET Directional TOPO Expression Kit (manufactured by Life Technologies Inc.), and transformed into a One Shot TOP10 strain. Positive clones were selected by colony PCR and cultured in an LB liquid medium containing 100 mg/L of ampicillin at a temperature of 37° C. and 200 rpm for 17 to 20 hours, and then plasmids were prepared using a miniprep kit (Wizard plus SV Minipreps DNA Purification System, manufactured by Promega Corporation). Sequence confirmation of the prepared plasmids was performed using a sequencer (3730 DNA Analyzer, manufactured by Life Technologies Corporation).

The gene clone AR19M-177-21 was obtained from the open reading frame AR19M-177 by PCR cloning. The nucleotide sequence of the gene clone AR19M-177-21, which is a xylanase candidate gene, was completely identical with the open reading frame AR19M-177 (SEQ ID NO: 2), and encoded a polypeptide (AR19M-177-21) composed of 355 amino acid residues (SEQ ID NO: 1).

FIG. 1 shows the alignment of the amino acid sequence of the gene clone AR19M-177-21 and the amino acid sequence (SEQ ID NO: 6) of the endo-1,4-β-xylanase from the bacterium *Thermotoga* sp. RQ2 of the phylum Thermotogae. In FIG. 1, the amino acids shown in white on black are the amino acid residues identical to both amino acid sequences, and "-" indicates a gap in a sequence.

<7> Gene Expression and Purification of Xylanase Enzyme Protein

Following sequence confirmation, the plasmid having the target gene was introduced into *E. coli* for protein expression using the heat shock method. The BL21 Star (DE3) strain provided in the Champion pET Directional TOPO Expression Kit (manufactured by Life Technologies Inc.) was used as the competent cell for the transformation. Expression of the target protein was induced by inoculating the *E. coli* having the target gene into an LB medium containing 100 mg/L of ampicillin, culturing to about $OD_{600}$=0.2 to 0.8, subsequently adding IPTG (isopropyl-β-D(−)-thiogalactopyranoside), and performing additional culturing for 5 to 20 hours. Following completion of the culturing, the *E. coli* was collected by centrifugation, and an amount of 50 mM Tris-HCl buffer (pH 8.0) equivalent to 1/10 of the volume of the culture liquid was then added and suspended. Subsequently, a process consisting of 5 minutes disrupting and then 5 minutes of rest was repeated 7 or 8 times using an ultrasonic disrupter Astrason 3000 (manufactured by MISONIX Inc.), thus obtaining a crude extract of the gene recombinant *E. coli* containing the target protein. This gene recombinant *E. coli* crude extract was filtered through a filter (pore size ϕ=0.45 μm, manufactured by EMD Millipore Corporation), and the resulting filtrate was used as a gene recombinant *E. coli* homogeneous supernatant.

The gene recombinant *E. coli* homogeneous supernatant was loaded onto an ion exchange column HiTrap Q HP (manufactured by GE Healthcare, Inc.) equilibrated with 50 mM Tris-HCl buffer (pH 8.0), and a medium-high pressure liquid chromatography system AKTA design (manufactured by GE Healthcare, Inc.) was used to fractionate proteins with a concentration gradient of 0 to 50% in 50 mM Tris-HCl buffer (pH 8.0) containing 1 M of NaCl. The fractions exhibiting xylanase activity were pooled, and a centrifugal ultrafiltration membrane VIVASPIN 20 (manufactured by Sartorius stedim Biotech SA) was used to exchange the buffer to a 50 mM Tris-HCl buffer (pH 8.0) containing 750 mM of ammonium sulfate. The fractions with xylanase activity following the buffer exchange were loaded onto a hydrophobic interaction separation column HiTrap Phenyl HP (manufactured by GE Healthcare, Inc.) equilibrated with the same solution, and the proteins were fractionated with a concentration gradient of 0 to 100% in 50 mM Tris-HCl buffer (pH 8.0). The fractions exhibiting xylanase activity were pooled and then concentrated using the VIVASPIN 20 until the liquid volume reached about 8 mL. The concentrated sample was loaded onto a gel filtration column Hiload 26/60 superdex 200 pg (manufactured by GE Healthcare, Inc.) equilibrated with 50 mM Tris-HCl buffer (pH 8.0) containing 150 mM of NaCl, and was fractionated by passing a volume of the same buffer equivalent to 1 to 1.5 times the column volume through the column at a flow rate of 2 to 3 mL/min. The fractions exhibiting xylanase activity were pooled, subjected to a buffer exchange into 50 mM Tris-HCl buffer (pH 8.0) and then concentrated, thus yielding a purified enzyme having a final concentration of about 1 mg/mL.

The gene recombinant *E. coli* homogenous supernatant and the purified enzyme were checked by SDS-PAGE (SDS-polyacrylamide gel electrophoresis) analysis. The SDS-PAGE of the gene recombinant *E. coli* homogenous supernatant and the purified enzyme was performed using a Mini-PROTEAN TGX Stain-Free gel (manufactured by Bio-Rad Laboratories, Inc.). The supernatant or the purified enzyme were each mixed with Tris-SDS βME treatment solution (manufactured by Cosmo Bio Co. Ltd.) at 1:1, and following treatment of the thus obtained samples at 100° C. for 10 minutes. Then, 10 of the gene recombinant *E. coli* homogenous supernatant and 1 μg of the purified enzyme were respectively electrophoresed. After the electrophoresis, the protein bands were visualized by CBB staining.

FIG. 2 shows the SDS-PAGE analysis results of the gene recombinant *E. coli* homogenous supernatant prepared from the transformed *E. coli* into which the AR19M-177-21 had been introduced, and the purified enzyme produced from the gene recombinant *E. coli* homogenous supernatant. The figure shows an electrophoretic pattern in which lane 1 represents a protein mass marker, lane 2 represents the gene recombinant *E. coli* homogenous supernatant, and lane 3 represents the purified enzyme. The results revealed a strong band in the gene recombinant *E. coli* homogenous supernatant (lane 2) near the mass of 41.1 kDa expected from the amino acid sequence (SEQ ID NO: 1), and a single band corresponding with this band (indicated by an arrow in the figure) was observed in the purified enzyme (lane 3).

<8> Measurement of Xylanase Activity (Xylan Hydrolysis Activity)

Xylan (derived from beechwood, manufactured by Sigma-Aldrich Co. LLC.) was used as the substrate for measuring the xylanase activity. A solution prepared by dissolving the xylan in water to obtain a concentration of 1% by mass relative to the total mass (hereafter sometimes referred to as a "1% by mass aqueous solution of xylan") was used as the substrate solution. The xylan substrate solutions used in the experiments described below all used the 1% by mass aqueous solution of xylan prepared by the above method.

The xylanase activity of the enzyme protein (AR19M-177-21) encoded by the AR19M-177-21 gene was investigated. Specifically, a mixed solution containing 100 μL of the 1% by mass aqueous solution of xylan, 50 μL of a 200 mM phosphate buffer (pH 6.0), either 50 μL of the gene recombinant *E. coli* homogenous supernatant obtained in section <7> above or 2 μL of the purified enzyme diluted with 50 mM Tris-HCl buffer (pH 8.0) (0.1 mg/mL), and 48 μL of purified water was reacted at 40 to 99° C. for 15 minutes. During the reaction, in order to prevent xylan precipitation, the mixed solution was stirred using an Eppendorf Thermomixer (1,400 rpm). In all measurements, a mixed solution prepared by replacing the gene recombinant *E. coli* homogenous supernatant or the purified enzyme with 50 mM Tris-HCl buffer (pH 8.0) and then reacting the solution under the same conditions was used as a control. Further, the substrate solution and the enzyme (the gene recombinant *E. coli* homogenous supernatant or the purified enzyme) were held separately at the reaction temperatures for 5 minutes before being mixed to initiate the reaction. Following completion of the reaction, 3,5-dinitrosalicylic acid reagent (DNS solution) was added to each mixed solution in a volume equal to that of the mixed solution, and the resulting mixture was heated at 100° C. for 5 minutes, cooled on ice for 5 minutes, and then centrifuged at 17,400 g for 5 minutes to obtain a supernatant. The absorbance at 540 nm was measured using a spectrophotometer, the amount of reduced sugar in the supernatant was calculated using a calibration curve prepared with xylose, and the amount of reduced sugar produced by the enzymatic hydrolysis was calculated from the difference from the control. The enzymatic activity for producing 1 μmol of reduced sugar per minute was defined as 1 U, and the value obtained by dividing this activity by the amount of protein was defined as the specific activity (U/mg).

As a result, xylanase activity was confirmed both in the case when the gene recombinant *E. coli* homogenous supernatant was used and the case when the purified enzyme was used.

<9> Substrate Specificity of AR19M-177-21

The hydrolysis activity of the enzyme protein (AR19M-177-21) encoded by the AR19M-177-21 gene against various cellulose substrates and hemicellulose substrates was investigated. In the measurements, a purified enzyme solution (0.1 mg/mL) obtained by diluting the purified enzyme (about 1 mg/mL) obtained in section <7> above with 50 mM Tris-HCl buffer (pH 8.0) was used. For the substrates, PSA, Avicel powder (microcrystalline cellulose powder, manufactured by Merck & Co., Inc.), CMC (manufactured by Sigma-Aldrich Co. LLC.), xylan (derived from beechwood, manufactured by Sigma-Aldrich Co. LLC.), lichenan (manufactured by MP Biomedicals Inc.), laminarin (derived from Laminaria digitata, manufactured by Sigma-Aldrich Co. LLC.), PNPX (manufactured by Sigma-Aldrich Co. LLC.) and PNPG (manufactured by Sigma-Aldrich Co. LLC.) were used.

The PSA was prepared by first dissolving Avicel powder (microcrystalline cellulose powder, manufactured by Merck & Co., Inc.) in a phosphoric acid solution, subsequently adding purified water to effect precipitation, and then performing washing until a pH of 5 or higher was reached. All the PSA used in the following experiments was prepared by this method.

Specifically, first, a reaction solution composed of a mixed solution containing 50 μL of 200 mM phosphate buffer (pH 6.0), 2 μL of the purified enzyme solution (0.1 mg/mL) and 48 μL of purified water was preincubated at 85° C. for 5 minutes, 100 μL of one of the substrate solutions (a 1% by mass aqueous solution in the case of PSA, Avicel powder, CMC, lichenan or laminarin, or a 20 mM aqueous solution in the case of PNPX or PNPG) that had been held at 85° C. was then added, and the enzyme reaction was performed by incubating the mixed solution at 85° C. for 15 minutes. During the reaction, the mixed solution was agitated at 1400 rpm using a Thermomixer (manufactured by the Eppendorf AG) so as to avoid the precipitation of insoluble substrate.

Following completion of the reaction, in the case of those reactions performed using PSA, Avicel powder, CMC, xylan, lichenan or laminarin as the substrate, the same method as that described in section <8> above for investigating the xylanase activity of AR19M-177-21 was used to measure the absorbance at 540 nm of the supernatant of the reacted mixed solution, subsequently determine the amount of reduced sugars produced by the hydrolysis, and then calculate the specific activity (U/mg). However, the amount of reduced sugars produced by hydrolysis of those substrates other than xylan was determined using a calibration curve prepared with glucose. In the case of the reactions performed using PNPG or PNPX as the substrate, following completion of the reaction, the reaction was stopped by adding the same volume of a 0.2 M aqueous solution of $Na_2CO_3$ to the mixed solution, and the resulting mixture was then centrifuged to obtain a supernatant. The amount of p-nitrophenol in the supernatant was determined by measuring the absorbance at 420 nm using a spectrophotometer, calculating the amount of p-nitrophenol in the supernatant using a calibration curve prepared with p-nitrophenol, and then determining the amount of p-nitrophenol produced by the enzymatic hydrolysis by the difference from the control. The enzymatic activity for producing 1 μmol of p-nitrophenol per minute was defined as 1 U, and the value obtained by dividing this activity by the amount of protein was defined as the specific activity (U/mg).

Figure 3:
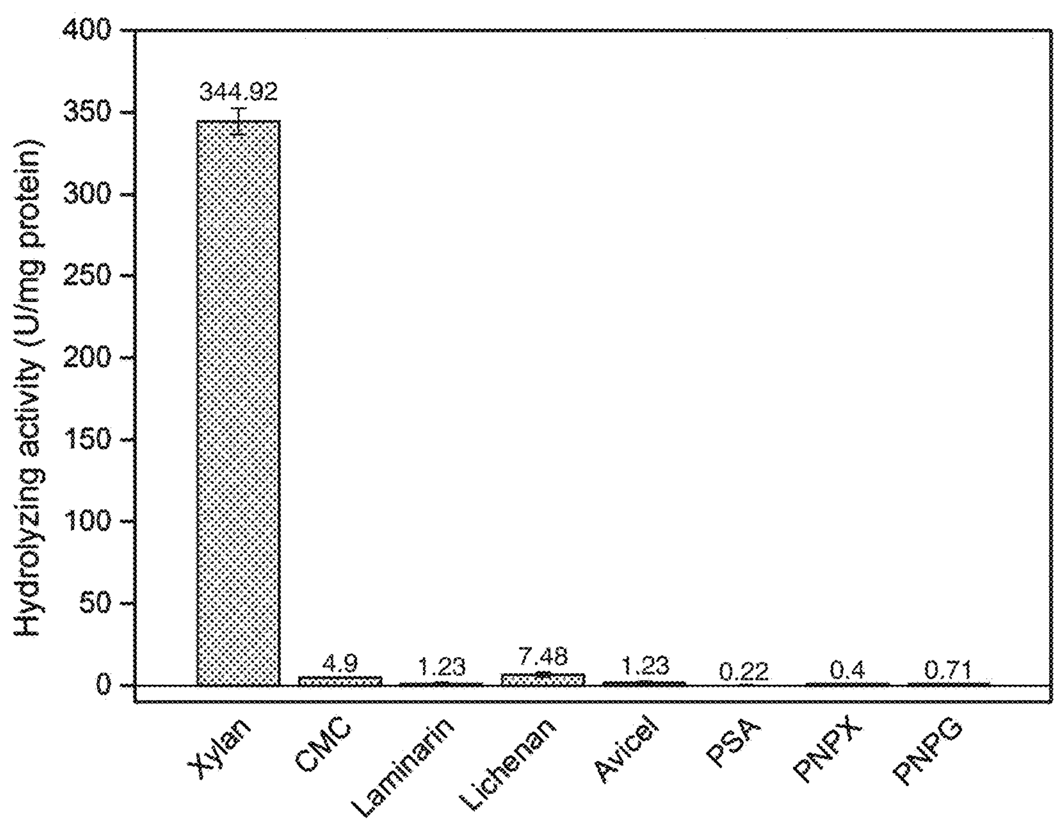
FIG. 3 is a diagram showing the results of measuring the xylanase activity of the AR19M-177-21 protein expressed in *E. coli* relative to various substrates in Example 1.

Each measurement was performed for three independent experiments, and a mean value and a standard error were determined. The measurement results are shown in FIG. 3. The results revealed that AR19M-177-21 exhibited a high level of hydrolysis activity against xylan. On the other hand, AR19M-177-21 exhibited almost no degradation activity against the other substrates.

<10> Temperature and pH Dependencies of Xylanase Activity Using Xylan as a Substrate The temperature dependency and the pH dependency of the xylanase activity of the enzyme protein (AR19M-177-21) encoded by the AR19M-177-21 gene were investigated. In the measurements, a purified enzyme solution obtained by diluting the purified enzyme (about 1 mg/mL) obtained in section <7> above to a concentration of 0.1 mg/mL with 50 mM Tris-HCl buffer (pH 8.0) was used.

Measurement of the temperature dependency of the xylanase activity of the purified AR19M-177-21 was conducted in the same manner as that described in section <8> above, with the exception of performing measurements at reaction temperatures of 40, 50, 60, 70, 75, 80, 85, 90, 95 and 99° C., and for each temperature, the amount of reduced sugars produced by the hydrolysis was determined, and the xylanase activity (U/mg) was calculated.

Measurement of the pH dependency of the xylanase activity of the purified AR19M-177-21 was conducted in the same manner as that described in section <8> above, with the exception of reacting a mixed solution containing 100 μL of a 1% by mass aqueous solution of xylan, 50 μL of McIlvaine's buffer (pH 3 to 8), 48 μL of purified water and 2 μL of the purified enzyme solution (0.1 mg/mL) at 85° C. for 15 minutes, and the amount of reduced sugars produced by the hydrolysis was determined and the xylanase activity (U/mg) was calculated for each of the pH values.

Figure 4:
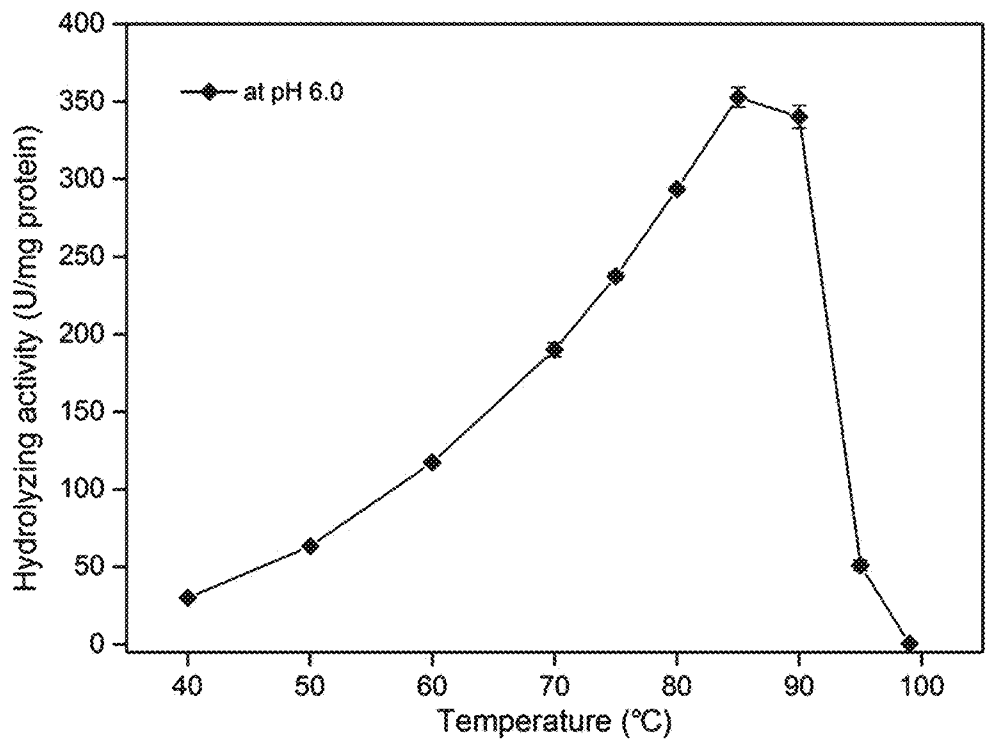
FIG. 4 is a diagram showing the results of measuring the xylanase activity (pH 6.0) of the AR19M-177-21 protein expressed in *E. coli* at various temperatures in Example 1.
Figure 5:
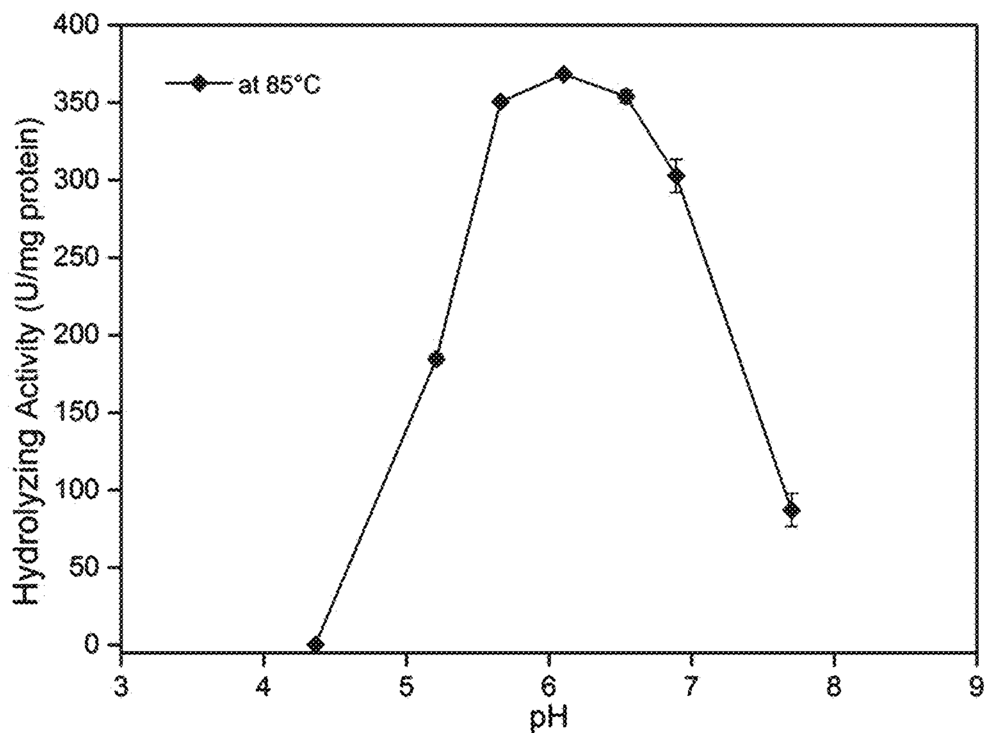
FIG. 5 is a diagram showing the results of measuring the xylanase activity (85° C.) of the AR19M-177-21 protein expressed in *E. coli* at various pH values in Example 1.

The measurement results are shown in FIG. 4 and FIG. 5. FIG. 4 is a graph showing the measurement results for the xylanase activity (pH 6.0) of the purified enzyme AR19M-177-21 at various temperatures, wherein the horizontal axis represents the temperature, and FIG. 5 is a graph showing the measurement results for the xylanase activity (85° C.) of the purified enzyme AR19M-177-21 at various pH values, wherein the horizontal axis represents the pH. For the pH, the actual measurement value obtained for the mixed solution containing the substrate, the buffer and the enzyme was plotted.

The purified enzyme AR19M-177-21 exhibited xylanase activity in a temperature range from 40 to 95° C. (FIG. 4). The optimum temperature ($T_{opt}$) showing the highest activity was 85° C. at a pH 6.0. When the enzymatic reaction temperature was set to 95° C. or higher, the xylanase activity of AR19M-177-21 decreased rapidly.

Moreover, the purified enzyme AR19M-177-21 exhibited xylanase activity in a pH range from 5.0 to 8.0 at a reaction temperature of 85° C. The optimum pH for the purified enzyme AR19M-177-21 at 85° C. was pH 6.1 (actual measurement value obtained for the mixed solution containing the substrate, the buffer and the enzyme).

<11> Thermal Stability Measurement of Xylanase by Differential Scanning Fluorimetry Differential scanning fluorimetry (DSF) is one of the methods of measuring the thermal denaturation of proteins using a fluorescent dye and a real-time PCR machine, and can be applied to all manner of proteins. The fluorescent dyes used in DSF such as SYPRO Orange emit fluorescence under nonpolar conditions when bound to a hydrophobic region, while the emission is suppressed under the polar conditions produced upon dissolution in water. Usually, the protein structure unfolds at the thermal denaturation temperature, and the hydrophobic regions of the protein are exposed at the protein surface. When SYPRO Orange binds to such an exposed hydrophobic region, excitation light having a wavelength of 470 to 480 nm causes emission of a strong fluorescence having a peak near a wavelength of 595 nm. By increasing the temperature of the protein solution at regular intervals in a stepwise manner and measuring the fluorescence intensity, the thermal degradation temperature (=change point of the fluorescence intensity) can be calculated.

Measurements were performed using the purified enzyme (1 mg/mL) obtained in section <7> above.

Specifically, 2 μL of 100-fold diluted SYPRO Orange (manufactured by Life Technologies Inc.), 1 μL of the purified enzyme with a concentration of 1 mg/mL, 5 μL of 200 mM phosphate buffer (pH 6.0) and 12 μL of purified water were added to each well of a 96-well PCR plate (Multiplate 96 Well PCR Plate MLL-9651, manufactured by Bio-Rad Laboratories, Inc.) so that the volume in each well was 20 μL. The PCR plate was sealed with Optical Flat 8-Cap Strips (manufactured by Bio-Rad Laboratories, Inc.), the temperature of each well was increased in steps of 0.2° C. from 30° C. up to 100° C. using a real-time PCR machine (CFX96 Touch Real-Time PCR System, manufactured by Bio-Rad Laboratories, Inc.), and following a pause of 10 seconds after each target temperature was achieved, the fluorescence intensity of each well was measured simultaneously. The SYPRO Orange was excited by a light emitting diode (LED) having a wavelength range of 450 to 490 nm, the emitted light from the SYPRO Orange was passed through a band pass filter having a range of 560 to 580 nm, a CCD camera was used to measure the fluorescence intensity, and the change in fluorescence intensity was plotted as a function of temperature. Data analysis was conducted using the analysis software CFX Manager (manufactured by Bio-Rad Laboratories, Inc.) supplied with the real-time PCR machine. Each measurement was performed for three independent experiments.

Figure 6:
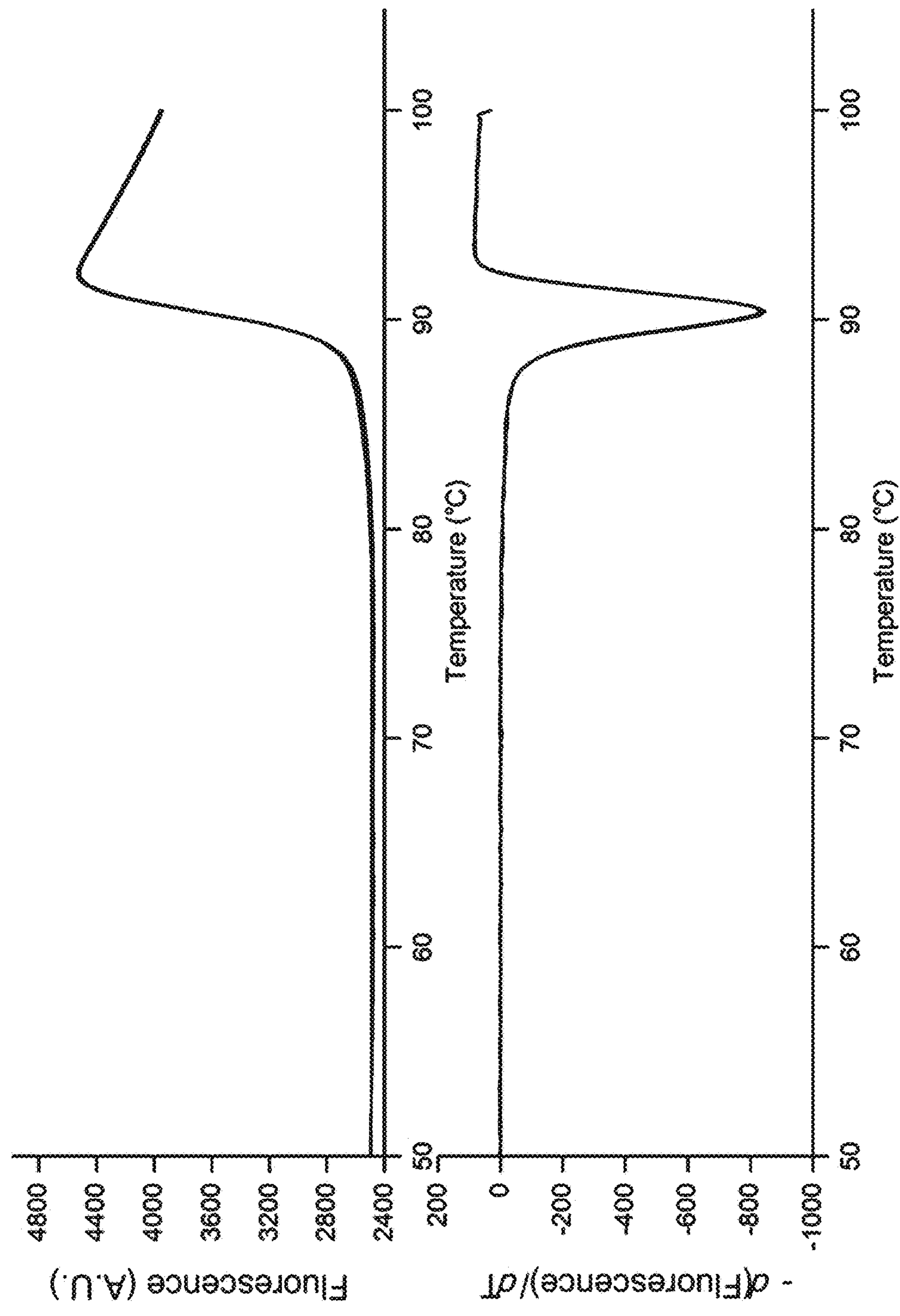
FIG. 6 is a diagram illustrating the change in the fluorescence intensity of SYPRO Orange caused in association with the thermal denaturation exhibited by the AR19M-177-21 protein expressed in *E. coli* in Example 1.

FIG. 6 shows the change in the fluorescence intensity of SYPRO Orange measured by the DSF method and caused in association with the thermal denaturation exhibited by the AR19M-177-21 enzyme protein. The upper graph in FIG. 6 shows the actual measurement data, and the lower graph in FIG. 6 shows the first derivative "-d(Fluorescence)/dt" of the fluorescence intensity change curve of the upper graph. The thermal denaturation temperature (melting temperature; Tm) was defined as the value at the local minimum of the first derivative of the fluorescence intensity curve (namely, "-d(Fluorescence)/dt" shown along the Y axis of the lower graph in FIG. 6). The first derivative of the fluorescence intensity for the AR19M-177-21 enzyme protein showed a negative peak near 90° C., indicating that thermal denaturation occurs at that temperature. The average Tm value of the AR19M-177-21 enzyme protein was 90.4° C.±0.0 (n=3), which was close to the optimum temperature $T_{opt}$=85° C. of the enzyme determined from the xylanase activity.

The invention claimed is:

1. A thermostable xylanase comprising an isolated polypeptide consisting of the amino acid sequence of SEQ ID NO: 1, and at least one region selected from the group consisting of a signal peptide added at the N-terminal or the C-terminal of the thermostable xylanase, and a tag added at the N-terminal or the C-terminal of the thermostable xylanase.

2. The thermostable xylanase according to claim 1, which exhibits xylanase activity at pH 6.0 and a temperature of 60 to 90° C.

3. A polynucleotide comprising a nucleotide sequence encoding an isolated polypeptide consisting of the amino acid sequence of SEQ ID NO: 1, and a nucleotide sequence encoding at least one region selected from the group consisting of a signal peptide added at the N-terminal or the C-terminal of the thermostable xylanase, and a tag added at the N-terminal or the C-terminal of the thermostable xylanase.

4. The polynucleotide according to claim 3, wherein the polypeptide exhibits xylanase activity at pH 6.0 and a temperature of 60 to 90° C.

5. An expression vector incorporating the polynucleotide according to claim 3, the expression vector being capable of expressing a polypeptide having xylanase activity in a host cell.

6. A transformant into which the expression vector according to claim 5 has been introduced.

7. The transformant according to claim 6, which is a eukaryote.

8. A method for producing a thermostable xylanase, the method comprising generating the thermostable xylanase in the transformant according to claim 6.

9. A glycoside hydrolase mixture, comprising the thermostable xylanase according to claim 1 and at least one other glycoside hydrolase.

10. A glycoside hydrolase mixture, comprising a thermostable xylanase encoded by the polynucleotide according to claim 3 and at least one other glycoside hydrolase.

11. A glycoside hydrolase mixture, comprising a thermostable xylanase produced by the method for producing a thermostable xylanase according to claim 8 and at least one other glycoside hydrolase.

12. A method for producing a lignocellulose degradation product, the method comprising generating the lignocellulose degradation product by bringing a lignocellulose-containing material comprising hemicellulose including xylan into contact with the thermostable xylanase according to claim 1.

13. A method for producing a lignocellulose degradation product, the method comprising generating the lignocellulose degradation product by bringing a lignocellulose-containing material comprising hemicellulose including xylan into contact with a thermostable xylanase encoded by the polynucleotide according to claim 3.

14. A method for producing a lignocellulose degradation product, the method comprising generating the lignocellulose degradation product by bringing a lignocellulose-containing material comprising hemicellulose including xylan into contact with the transformant according to claim 6.

15. A method for producing a lignocellulose degradation product, the method comprising generating the lignocellulose degradation product by bringing a lignocellulose-containing material comprising hemicellulose including xylan into contact with a thermostable xylanase produced by the method for producing a thermostable xylanase according to claim 8.

16. A method for producing a lignocellulose degradation product, the method comprising generating the lignocellulose degradation product by bringing a lignocellulose-containing material comprising hemicellulose including xylan into contact with the glycoside hydrolase mixture according to claim 9.

17. A method for producing a lignocellulose degradation product, the method comprising generating the lignocellulose degradation product by bringing a lignocellulose-containing material comprising hemicellulose including xylan into contact with the glycoside hydrolase mixture according to claim 10.

18. A method for producing a lignocellulose degradation product, the method comprising generating the lignocellulose degradation product by bringing a lignocellulose-containing material comprising hemicellulose including xylan into contact with the glycoside hydrolase mixture according to claim 11.

* * * * *

SEQUENCE LISTING

```
<160> NUMBER OF SEQ ID NOS: 6

<210> SEQ ID NO 1
<211> LENGTH: 355
<212> TYPE: PRT
<213> ORGANISM: Unknown
<220> FEATURE:
<223> OTHER INFORMATION: Amino acid sequence of AR19M-177-21; present in
      natural; obtained from a microorganism which lives in high
      temperature hot spring soils; has a homology with an amino acid
      sequence of the endo-1,4-beta-xylanase belonging to GH10 family

<400> SEQUENCE: 1

Met Gly Val Lys Ser Val Lys Lys Leu Leu Val Ala Phe Leu Leu Ser
1               5                   10                  15

Leu Leu Thr Leu Gly Leu Ala Ser Asn Gly Leu Glu Gly Glu Thr Leu
            20                  25                  30

Arg Ser Leu Ala Glu Lys Leu Gly Ile Tyr Val Gly Phe Ala Ser Ile
        35                  40                  45

Asn Asn Phe Trp Val Leu Ala Asp Gly Ser Thr Tyr Met Glu Val Ala
    50                  55                  60

Lys Arg Glu Phe Asn Ile Leu Thr Pro Glu Asn His Met Lys Trp Asp
65                  70                  75                  80

Ser Ile His Pro Glu Arg Asp Arg Tyr Asp Phe Ser Lys Ala Glu Arg
                85                  90                  95

His Val Lys Phe Ala Leu Glu Asn Gly Met Val Val His Gly His Thr
            100                 105                 110

Leu Val Trp His Asn Gln Leu Pro Pro Trp Leu Asn Lys Glu Trp Thr
        115                 120                 125

Lys Glu Glu Leu Leu Gln Val Leu Glu Glu His Ile Lys Thr Val Val
    130                 135                 140

Gly Tyr Phe Lys Gly Lys Val Lys Ile Trp Asp Val Val Asn Glu Ala
145                 150                 155                 160

Val Ser Asp Ala Gly Arg Tyr Arg Glu Thr Ile Trp Tyr Lys Val Ile
                165                 170                 175

Gly Pro Glu Tyr Ile Glu Lys Ala Phe Ile Trp Ala Arg Glu Ala Asp
            180                 185                 190

Pro Asp Ala Thr Leu Ile Tyr Asn Asp Tyr Asn Ile Glu Thr Ile Asn
        195                 200                 205

Pro Lys Ser Asn Phe Val Tyr Gln Leu Val Lys Glu Leu Lys Glu Lys
    210                 215                 220

Gly Val Pro Ile Asp Gly Val Gly Phe Gln Met His Ile Asp Ile Asn
```

```
225                 230                 235                 240

Gly Ile Asn Tyr Glu Ser Phe Arg Asn Asn Leu Lys Arg Phe Ala Asp
                245                 250                 255

Leu Gly Leu Lys Leu Tyr Ile Thr Glu Met Asp Val Arg Ile Pro Lys
            260                 265                 270

Asn Ala Thr Gln Glu His Leu Gln Lys Gln Ala Glu Ile Tyr Ala Lys
        275                 280                 285

Ile Phe Glu Ile Cys Leu Glu Asn Pro Ala Val Glu Ala Ile Gln Phe
    290                 295                 300

Trp Gly Phe Thr Asp Lys Tyr Ser Trp Val Pro Gly Phe Phe Thr Gly
305                 310                 315                 320

Tyr Asp His Ala Leu Ile Phe Asp Arg Asp Tyr Asn Pro Lys Pro Ala
                325                 330                 335

Tyr Phe Ala Ile Lys Gln Val Leu Ala Lys Lys Leu Glu Glu Lys Leu
            340                 345                 350

Lys Gly Lys
        355
```

<210> SEQ ID NO 2
<211> LENGTH: 1068
<212> TYPE: DNA
<213> ORGANISM: Unknown
<220> FEATURE:
<223> OTHER INFORMATION: Nucleotide sequence (i.e., open reading frame) of AR19M-177-21; present in natural; obtained from a microorganism which lives in high temperature hot spring soils

<400> SEQUENCE: 2

```
atgggggtga agagcgtgaa aaaactgctg gttgcgtttc tgttgtctct tttgacattg     60

ggacttgcat cgaacggatt ggagggagaa actttgagat ccttagcgga aaagttggga    120

atctacgtcg gttttgcgtc gatcaacaac ttctgggtcc tcgcagatgg cagcacgtac    180

atggaggttg caaagcgaga gttcaacata ctgacgcctg agaaccacat gaagtgggac    240

agcatacacc cggagcgtga caggtacgat ttttcgaagg ccgaaagaca cgtcaagttc    300

gcgctcgaga acggcatggt cgtccacggt cacaccttag tctggcacaa ccagctccca    360

ccctggttga acaaggaatg gacgaaagaa gaactgctcc aggttcttga agaacatata    420

aagacagtcg tgggatattt caaaggaaaa gtcaagatat gggacgttgt gaacgaggcg    480

gtcagcgacg ctgggaggta ccgggaaacg atctggtaca aagtcatagg cccggagtac    540

atagaaaagg ccttcatctg ggccagggaa gcggatccag acgccactct catatacaac    600

gactacaaca tagaaacgat caatcccaag tcgaatttcg tttaccagct cgtgaaagag    660

ctcaaagaga agggcgtacc gatcgacggc gtgggctttc agatgcacat agacatcaac    720

gggatcaact acgagagctt caggaacaat ttgaagaggt ttgccgacct gggactcaaa    780

ctctacatca ccgagatgga cgtgaggatt cccaaaaacg ccacgcagga gcatctacaa    840

aagcaggccg agatatacgc gaaaatattc gaaatctgcc tcgaaaatcc ggcggtcgaa    900

gccatacagt tctggggctt caccgacaaa tactcctggg tgccgggctt cttcacaggc    960

tacgatcacg ctctgatttt cgacagagac tacaatccca aacctgcgta cttcgcgata   1020

aaacaggttc ttgcgaagaa gctggaagaa aagctgaagg gtaaatga                1068
```

<210> SEQ ID NO 3
<211> LENGTH: 21
<212> TYPE: DNA
<213> ORGANISM: Artificial Sequence
<220> FEATURE:
<223> OTHER INFORMATION: Primer; nucleotide sequence which is homologous (identical) with a partial sequence composed of the nucleotides from positions 1 to 21 of the nucleotide sequence of SEQ ID NO: 2; artificially synthesized

<400> SEQUENCE: 3
atgggggtga agagcgtgaa a 21

<210> SEQ ID NO 4
<211> LENGTH: 21
<212> TYPE: DNA
<213> ORGANISM: Artificial Sequence
<220> FEATURE:
<223> OTHER INFORMATION: Reverse primer which is complementary with a partial sequence composed of the nucleotides from positions 1048 to 1068 of the nucleotide sequence of SEQ ID NO: 2; primer for gene cloning; artificially synthesized

<400> SEQUENCE: 4
tcatttaccc ttcagctttt c 21

<210> SEQ ID NO 5
<211> LENGTH: 25
<212> TYPE: DNA
<213> ORGANISM: Artificial Sequence
<220> FEATURE:
<223> OTHER INFORMATION: Forward primer in which 4 nucleotides (CACC) are added to the 5'-end of the nucleotide sequence of SEQ ID NO: 3; primer for gene cloning; artificially synthesized

<400> SEQUENCE: 5
caccatgggg gtgaagagcg tgaaa 25

<210> SEQ ID NO 6
<211> LENGTH: 347
<212> TYPE: PRT
<213> ORGANISM: Unknown
<220> FEATURE:
<223> OTHER INFORMATION: Amino acid sequence of an endo-1,4-beta-xylanase belonging to the GH10 family of the bacterium Thermotoga sp. RQ2 of the phylum Thermotogae; present in natural;

<400> SEQUENCE: 6

```
Met Lys Ile Leu Pro Ser Val Leu Ile Leu Leu Leu Gly Cys Val Pro
1               5                   10                  15

Val Phe Ser Ser Gln Asn Val Ser Leu Arg Glu Leu Ala Glu Lys Leu
            20                  25                  30

Asn Ile Tyr Val Gly Phe Ala Ala Ile Asn Asn Phe Trp Ser Leu Ser
        35                  40                  45

Asp Ala Glu Lys Tyr Met Glu Val Ala Arg Arg Glu Phe Asn Ile Leu
    50                  55                  60

Thr Pro Glu Asn Gln Met Lys Trp Asp Thr Ile His Pro Glu Arg Asp
65                  70                  75                  80

Arg Tyr Asn Phe Thr Pro Ala Glu Lys His Val Glu Phe Ala Glu Glu
                85                  90                  95

Asn Asn Met Ile Val His Gly His Thr Leu Val Trp His Asn Gln Leu
            100                 105                 110

Pro Gly Trp Ile Thr Gly Arg Glu Trp Thr Lys Glu Glu Leu Leu Asn
        115                 120                 125

Val Leu Glu Asp His Ile Lys Thr Val Val Ser His Phe Lys Gly Arg
    130                 135                 140
```

-continued

```
Val Lys Ile Trp Asp Val Val Asn Glu Ala Val Ser Asp Ser Gly Thr
145                 150                 155                 160

Tyr Arg Glu Ser Ile Trp Tyr Lys Thr Ile Gly Pro Glu Tyr Ile Glu
                165                 170                 175

Lys Ala Phe Arg Trp Ala Lys Glu Ala Asp Pro Asp Ala Ile Leu Ile
            180                 185                 190

Tyr Asn Asp Tyr Ser Ile Glu Glu Ile Asn Ala Lys Ser Asn Phe Val
        195                 200                 205

Tyr Asn Met Ile Lys Glu Leu Lys Glu Lys Gly Val Pro Val Asp Gly
    210                 215                 220

Ile Gly Phe Gln Met His Ile Asp Tyr Arg Gly Leu Asn Tyr Asp Ser
225                 230                 235                 240

Phe Arg Arg Asn Leu Glu Arg Phe Ala Lys Leu Gly Leu Gln Ile Tyr
                245                 250                 255

Ile Thr Glu Met Asp Val Arg Ile Pro Leu Ser Gly Ser Glu Glu Tyr
            260                 265                 270

Tyr Leu Lys Lys Gln Ala Glu Val Cys Ala Lys Ile Phe Asp Ile Cys
        275                 280                 285

Leu Asp Asn Pro Ala Val Lys Ala Ile Gln Phe Trp Gly Phe Thr Asp
    290                 295                 300

Lys Tyr Ser Trp Val Pro Gly Phe Phe Lys Gly Tyr Gly Lys Ala Leu
305                 310                 315                 320

Leu Phe Asp Glu Asn Tyr Asn Pro Lys Pro Cys Tyr Tyr Ala Ile Lys
                325                 330                 335

Glu Val Leu Glu Lys Lys Ile Glu Glu Arg Lys
            340                 345
```